(12) United States Patent
Shimm

(10) Patent No.: US 6,805,699 B2
(45) Date of Patent: Oct. 19, 2004

(54) LAPAROSCOPIC SPECIMEN RETRIEVAL SHOEHORN

(76) Inventor: Peter Shimm, 4215 Thornapple St., Chevy Chase, MD (US) 20815

( * ) Notice: Subject to any disclaimer, the term of this patent is extended or adjusted under 35 U.S.C. 154(b) by 0 days.

(21) Appl. No.: 10/431,607

(22) Filed: May 8, 2003

(65) Prior Publication Data

US 2003/0216773 A1 Nov. 20, 2003

Related U.S. Application Data

(63) Continuation-in-part of application No. 10/125,495, filed on Apr. 19, 2002.

(51) Int. Cl.[7] ............................................. A61M 29/00
(52) U.S. Cl. ...................................... 606/200; 606/127
(58) Field of Search ................................ 606/200, 198, 606/113, 127, 108; 604/104–109

(56) References Cited

U.S. PATENT DOCUMENTS

| | | | |
|---|---|---|---|
| 3,717,151 A | * 2/1973 | Collett | ......................... 604/106 |
| 3,902,501 A | * 9/1975 | Citron et al. | ................ 607/126 |
| 5,183,465 A | * 2/1993 | Xanthakos et al. | .......... 604/108 |
| 5,263,937 A | * 11/1993 | Shipp | ..................... 604/166.01 |
| 5,320,627 A | 6/1994 | Sorensen et al. | |
| 5,370,647 A | 12/1994 | Graber et al. | |
| 5,417,684 A | 5/1995 | Jackson et al. | |
| 5,465,731 A | 11/1995 | Bell et al. | |
| 5,577,993 A | * 11/1996 | Zhu et al. | ................... 600/204 |
| 5,591,177 A | 1/1997 | Lehrer | |
| 5,643,313 A | 7/1997 | Levin | |
| 5,707,359 A | 1/1998 | Bufalini | |
| 5,788,709 A | 8/1998 | Reik et al. | |
| 5,797,906 A | 8/1998 | Rhum et al. | |
| 5,971,960 A | * 10/1999 | Flom et al. | .................. 604/174 |
| 5,980,544 A | 11/1999 | Vaitekunas | |
| 6,059,734 A | 5/2000 | Yoon | |
| 6,074,408 A | 6/2000 | Freeman | |
| 6,152,932 A | 11/2000 | Ternström | |
| 6,203,517 B1 | 3/2001 | Shipp et al. | |
| 6,206,889 B1 | 3/2001 | Bennardo | |
| 6,508,825 B1 | * 1/2003 | Selmon et al. | ............... 606/198 |

* cited by examiner

Primary Examiner—Tan-Uyen T. Ho
(74) Attorney, Agent, or Firm—Pillsbury Winthrop LLP

(57) ABSTRACT

An laparoscopic specimen retrieval shoehorn ("LSRS") is described. The LSRS has a primary shaft with a rearward portion, an intermediate portion, and a forward portion. The forward portion is radially-enlarged relative to the intermediate portion. A secondary shaft is slidably disposed within the primary shaft. The secondary shaft has an endo-bag attached thereto. A sheath having expanded and contracted positions is slidably disposed around the primary shaft. The sheath has a holding ring disposed radially-outwardly from the intermediate portion of the primary shaft. The holding ring is adapted to slide relative to the intermediate portion. The holding ring is disposed at a rear end of the sheath. A plurality of circumferentially-spaced prongs are disposed at a forward end of the sheath. During transition from the contracted to the expanded position of the sheath, the radially-enlarged forward portion expands the prongs radially-outwardly.

20 Claims, 24 Drawing Sheets

LAPAROSCOPIC SPECIMEN RETRIEVAL SHOEHORN

CROSS-REFERENCE TO RELATED APPLICATION(S)

This application is a Continuation-In-Part of U.S. patent application Ser. No. 10/125,495, entitled "LAPAROSCOPIC SPECIMEN EXTRACTION PORT," which was filed on Apr. 19, 2002, the contents of which are incorporated herein by reference.

BACKGROUND OF THE INVENTION

1. Field of the Invention

The present invention concerns the construction of a laparoscopic specimen retrieval shoehorn ("LSRS"). An LSRS combines the features and advantages of a laparoscopic specimen extraction port ("LSEP") with those of an endoscopic specimen retrieval bag device ("ERBD"). More specifically, the present invention concerns the construction of a device that facilitates removal of a specimen extracted from a patient during laparoscopic surgery, among other types of surgery.

2. Description of Related Art

As illustrated in FIG. 11, during a typical abdominal laparoscopic surgery, a surgeon makes four or so small (typically about 2 cm) incisions 10 in the abdominal wall 20 of the patient. The surgeon positions a trocar 22 (shown in FIGS. 15 and 16) into an axial hole 26 in a laparoscopic port 30 to facilitate insertion of the port 30 into the incision 10. After inserting the trocar 22 and port 30 through the incision 10, the surgeon removes the trocar 22 to allow insertion of surgical instruments (e.g., grasping instrument 80) into the abdominal cavity 40 through the axial hole 26 in the port 30. The surgeon repeats this procedure for each of the four or so required ports 30.

To simplify the figures and focus on the functional structures of the laparoscopic port 30 and trocar 22, FIGS. 11–14 illustrate simplified views of the conventional laparoscopic port 30. It is to be understood, however, that in reality, conventional laparoscopic ports 30 and trocars 22 are typically shaped as shown in FIGS. 15 and 16. Similar types of simplified views are used to illustrate the present invention. Nonetheless, as would be appreciated by one of ordinary skill in the art, the present invention will, in practice, have a shape similar to the laparoscopic port 30 and trocar 22 illustrated in FIGS. 15 and 16.

The surgical instruments that are inserted through the laparoscopic port 30 typically include a video camera that enables the surgeon to visualize the surgical procedure. Variously sized surgical ports 30 are designed to be used with variously sized instruments. Typical instruments require surgical ports 30 with axial holes 26 having 5 mm inside diameters. As is discussed in greater detail below, endoscopic specimen retrieval bags ("endo-bags™") typically are inserted through ports 30 that have holes 26 with 10 mm inside diameters and 12 mm outside diameters.

During laparoscopic surgery, the abdomen is insufflated with carbon dioxide to distend the abdominal cavity 40 (creating pneumoperitoneum) and allow for better visualization of the surgical operation. Each port 30 includes a flapper valve 45 (see FIGS. 15 and 16) that opens to allow the surgeon to insert an instrument therethrough and automatically closes when the instrument is removed so as to prevent the loss of pneumoperitoneum.

During laparoscopic surgery, it is often necessary to extract a specimen 50 such as a gall bladder from the abdominal cavity 40 of the patient. As illustrated sequentially in FIGS. 11–14, using a conventional specimen extraction technique, the surgeon inserts an endo-bag 60 through one of the ports 30 and positions the endo-bag 60 using an endo-bag handle/controller 70. As illustrated in FIG. 11, after the specimen 50 has been surgically detached from the patient, the surgeon uses a surgical grasping instrument 80, which is inserted into the abdominal cavity 40 through a separate port 30, to place the specimen into the open endo-bag 60. As illustrated in FIG. 12, the surgeon pulls a "purse string" 90 of the endo-bag 60 to synch down the open end of the endo-bag 60, thereby securely enclosing the specimen 50 within the endo-bag 60. As illustrated in FIG. 13, the surgeon then removes the port 30 through which the endo-bag 60 was inserted, leaving the purse string 90 extending through the incision 10. This unfortunately often causes loss of pneumoperitoneum, leading to impaired visualization of the specimen 50 during the extraction process. The surgeon thereafter attempts to pull the endo-bag 60 and specimen 50 out of the abdominal cavity 40 through the incision 10.

Unfortunately, as illustrated in FIG. 14, it is frequently difficult for the surgeon to extract the specimen 50 and endo-bag 60 through the relatively small incision 10. As the surgeon pulls the endo-bag 60 through the incision 10, most of the plastic endo-bag 60 easily pulls through the incision 10 with the specimen 50 bunching in the bottom of the endo-bag 60 in the abdominal cavity 40 (as shown in FIG. 14). Such bunching results in a variety of deleterious effects. In one example, the surgeon may resort to exerting a strong pulling force on the endo-bag 60, causing the endo-bag 60 and/or the surgical specimen 50 to rupture. Such a rupture might spread infectious, bilious, and/or even cancerous material in the abdominal wall 20 and cavity 40. Alternatively, the surgeon may resort to extending his/her initially relatively small port incision 10. Expanding the incision 10 deleteriously increases postoperative pain, increases surgical blood loss, increases the risk of future dehiscence (opening) of the incision and/or herniation of the abdominal contents through the expanded incision 10, and reduces or eliminates the advantages of laparoscopic surgery. Furthermore, the complications that often accompany the specimen 50 extraction procedure add significant operating room and anesthetic time to the surgery, which greatly increases the cost of the procedure to the hospital and the patient.

In summary, while prior art laparoscopic ports 30 and procedures(s) (as outlined above in connection with FIGS. 11–14) have proven effective, for the most part, in laparoscopic surgery, the prior art ports 30 available (and, therefore, the procedure(s) used in connection with those ports 30) may lead unnecessarily to complications. This has resulted in a need for an improved port and/or procedure to lessen the occurrence of such complications.

In addition, as may be apparent from the foregoing discussion, laparoscopic surgery relies upon coordination between several instruments, the port 30, the endo-bag handle/controller 70, the endo-bag 60, and the surgical grasping instrument 80. This coordination, while performed routinely and successfully during laparoscopic surgery, is complex and calls out for a solution.

SUMMARY OF THE INVENTION

One aspect of the present invention, therefore, provides an improved laparoscopic instrument that reduces surgery time and post-operative recovery time.

An additional aspect of the present invention provides a laparoscopic instrument that substantially prevents a specimen from bunching in an endo-bag during extraction of the specimen from a patient.

A further aspect of the present invention provides a laparoscopic instrument that reduces the risk of rupturing the specimen or endo-bag during extraction of the specimen from a patient.

A further aspect of the present invention provides a laparoscopic instrument that reduces the risk of spreading infectious, bilious, and/or cancerous material into the patient's abdominal cavity and/or incision.

Another aspect of the present invention is to provide an LSRS. The LSRS has a primary shaft, where the primary shaft includes a rearward portion, an intermediate portion, and a forward portion. The forward portion is radially-enlarged relative to the intermediate portion. A secondary shaft is slidably disposed within the primary shaft. The secondary shaft has an endo-bag attached thereto. A sheath, with expanded and contracted positions, is slidably disposed around the primary shaft. The sheath has a holding ring disposed radially-outwardly from the intermediate portion of the primary shaft. The holding ring is adapted to slide relative to the intermediate portion. The holding ring is disposed at a rear end of the sheath. A plurality of circumferentially-spaced prongs are disposed at a forward end of the sheath. The prongs have forward ends positioned adjacent to the radially-enlarged, forward portion of the primary shaft when in the contracted position. The forward ends of the prongs expand radially-outwardly relative to the primary shaft when the sheath is in the expanded position. During transition from the contracted to the expanded position, the radially-enlarged forward portion expands the prongs radially-outwardly.

A further aspect of the invention involves the construction of an LSRS where the prongs are shoehorn shaped.

Another aspect of the invention provides an LSRS where the prongs overlap one another at least partially when in the contracted position.

An additional aspect of the present invention provides an LSRS with a sheath having an intermediate shaft connecting the holding ring to the rearward ends of the prongs.

Still another aspect of the invention concerns the forward portion of the primary shaft, which is radially-enlarged relative to an inside surface of the holding ring such that the forward portion prevents the holding ring from sliding forwardly beyond the forward portion.

One additional aspect of the invention provides for an LSRS with a releasable holding mechanism to selectively secure the holding ring to the intermediate portion of the primary shaft when the sheath is in the contracted position.

An aspect of the invention also concerns an LSRS where rotation of the holding ring relative to the primary shaft disengages the holding mechanism to allow the sheath to be manipulated into the expanded position.

One further aspect of the invention concerns the holding mechanism for an LSRS. The holding mechanism has a forwardly-facing surface defined by the holding ring, a notch on an inside surface of the holding ring, the notch extending rearwardly from the forwardly-facing surface, and a protrusion extending from an outer surface of the intermediate portion of the primary shaft. A rearward edge of the protrusion is disposed in front of the forwardly-facing surface when the sheath is in the contracted position to prevent the sheath from moving rearwardly relative to the primary shaft. Rotation of the holding ring relative to the primary shaft aligns the protrusion with the notch, thereby allowing the protrusion to move through the notch and the primary shaft to move rearwardly relative to the holding ring to permit the sheath to be manipulated into the expanded position.

Another aspect of the invention is directed to an LSRS where the forward portion of the primary shaft comprises a radially-outwardly-tapering outer surface.

Still another aspect of the invention concerns an LSRS where each prong includes a forward tip that has inside and outside surfaces, and wherein the inside surface of the forward tip tapers radially-outwardly so that, when the sheath is in the contracted position, the outwardly-tapering inside surface of the forward tip of each prong adjoins the outwardly-tapering outer surface of the forward portion of the primary shaft.

Aspects of the invention also encompass an LSRS where the prongs comprise a flexible material that expands radially-outwardly during expansion of the laparoscopic specimen retrieval shoehorn.

Still other aspects of the present invention are directed to an LSRS where the prongs comprise at least one of plastic and PVC.

Additional aspects of the invention concern an LSRS where an indentation is formed on a surface of the sheath to define a folding line for the prongs.

Another aspect of the invention encompasses an LSRS where the prongs are tinted a color easily distinguishable from tissue or are partially radio-opaque.

One further aspect of the invention concerns an LSRS where the secondary shaft further includes a wire attached thereto. An endo-bag is disposed one the wire. The wire is pre-conditioned to form a loop.

One further aspect of the invention provides an LSRS where the wire has a cross-section selected from a group comprising rectangular, circular, elliptical, and ovoid.

Still another aspect of the invention is directed to an LSRS where the primary shaft and the secondary shaft define deployed and non-deployed positions with respect to one another. When in the deployed position, the endo-bag is disposed exteriorly to the primary shaft.

A further aspect of the invention encompasses an LSRS where the primary shaft and the secondary shaft define deployed and non-deployed positions with respect to one another. When in the deployed position, the wire and the endo-bag are disposed exteriorly to the primary shaft.

Still another aspect of the present invention is directed to an LSRS including a purse string attached to the endo-bag so that, after insertion of a specimen thereinto, the purse string may close an open end of the endo-bag.

One further aspect of the invention provides for an LSRS where the endo-bag is detachably connected to the secondary shaft such that, when the purse string is pulled, the endo-bag detaches from the secondary shaft and its open end is closed thereby.

Additional and/or alternative objects, features, aspects, and advantages of the present invention will become apparent from the following description, the accompanying drawings, and the appended claims.

BRIEF DESCRIPTION OF THE DRAWINGS

For a better understanding of the present invention as well as other objects and further features thereof, reference is made to the following description which is to be used in conjunction with the accompanying drawings, where.

DETAILED DESCRIPTION OF PREFERRED EMBODIMENTS OF THE INVENTION

Figure 1:
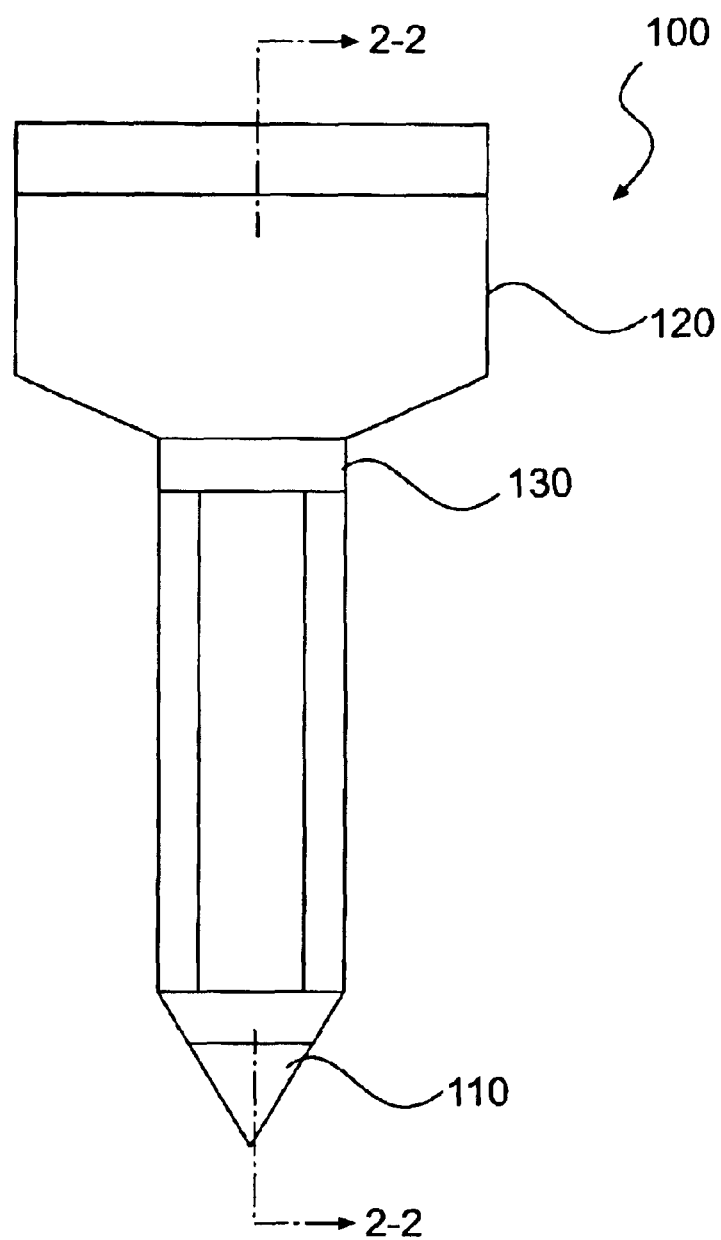
FIG. 1 is a side view of an LSEP according to one embodiment of the present invention.

FIG. 1 is a side view of an LSEP 100 according to the present invention. The LSEP 100 includes a pointed trocar 110, a port 120, and a sheath 130. The LSEP 100 has expanded and contracted positions.

Figure 2:
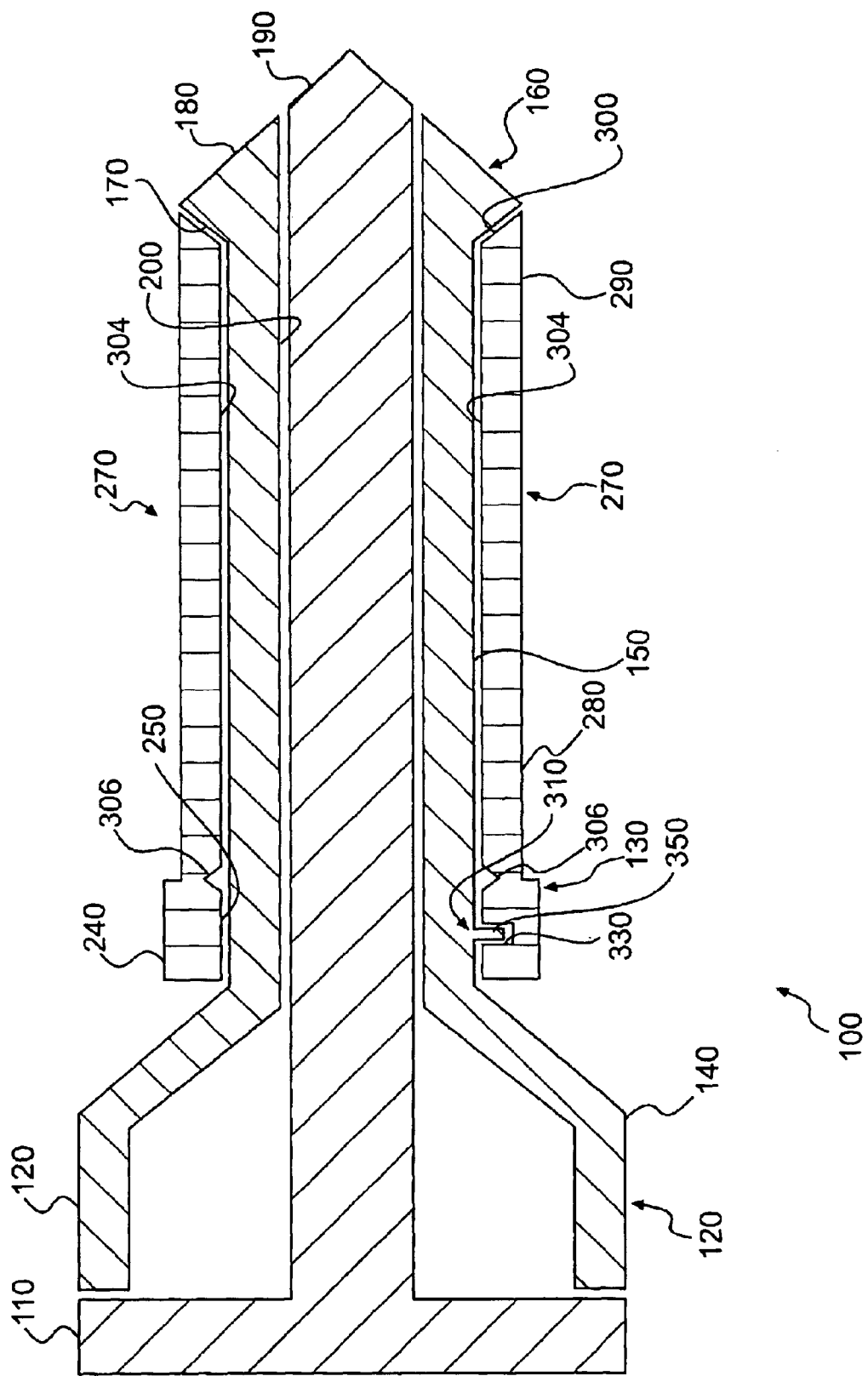
FIG. 2 is a cross-section of the LSEP illustrated in FIG. 1, taken along the line 2—2 in FIG. 1.
Figure 3:
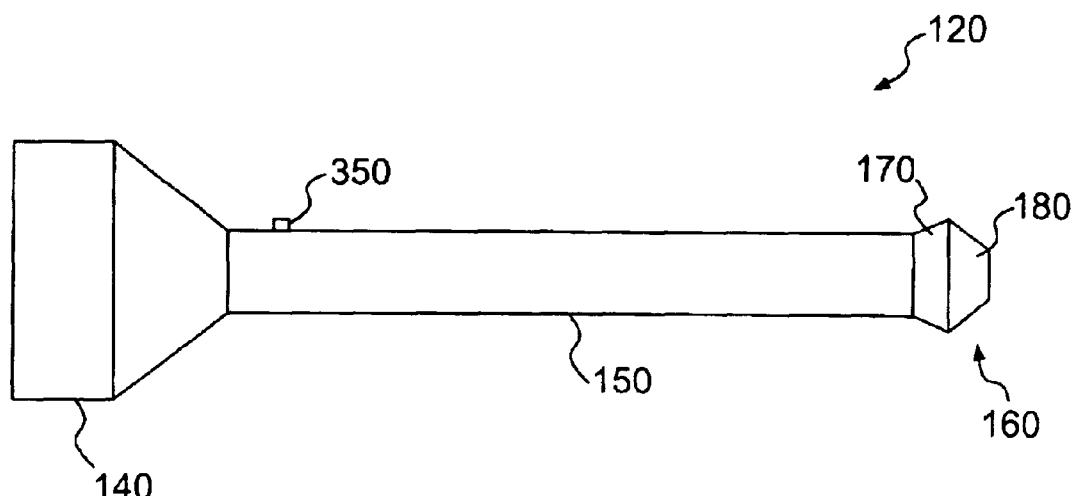
FIG. 3 is a side view of a port of the LSEP of FIG. 1.
Figure 15:
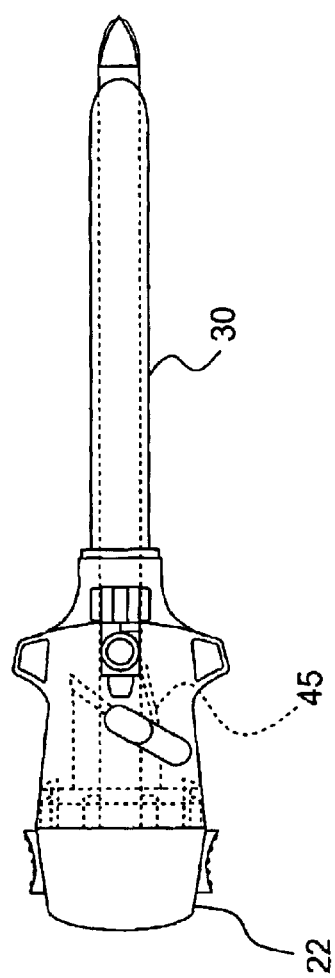
FIGS. 15 and 16 are side views showing an interaction between a conventional trocar and LSEP.
Figure 16:
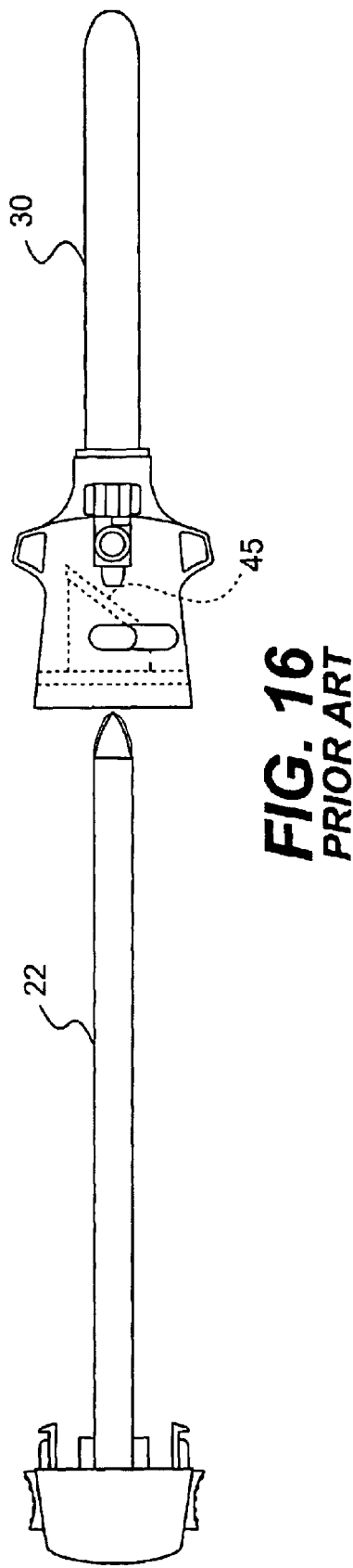

As illustrated in FIGS. 2 and 3, the port 120 is elongated and hollow. A rearward (or proximal) portion 140 of the port 120 is generally funnel-shaped and tapers radially-inwardly toward an intermediate portion 150. A flapper valve (not shown) like the conventional flapper valve 45 illustrated in FIGS. 15 and 16 is preferably disposed in the rearward portion 140 to preserve pneumoperitoneum during surgery when surgical instruments are not inserted through the port 120. The intermediate portion 150 is longitudinally elongated and preferably has a constant cross-section over its longitudinal length. As would be appreciated by one of ordinary skill in the art, however, the intermediate portion 150 need not have a constant cross-section over its longitudinal length. To the contrary, the cross-section may be tapered inwardly or outwardly along its length. In addition, the cross-section may vary over its longitudinal length. As would be appreciated by those of ordinary skill in the art, the precise configuration of the cross-section of the intermediate portion 150 is not critical to the operation of the present invention.

As illustrated in FIG. 3, a forward (or distal) portion 160 of the port 120 extends forwardly from the intermediate portion 150 and is radially-enlarged relative to the intermediate portion 150. The forward portion 160 includes an outer surface 170 that tapers radially-outwardly from a forward end of the intermediate portion 150. The outer surface 170 is preferably frustroconical but may alternatively form other shapes. The forward portion 160 also includes a forward tip 180 that tapers radially-inwardly from the forward edge of the outer surface 170. The inward taper of the forward tip 180 preferably matches an inward taper of an inwardly-tapering tip 190 of the trocar 110 such that when the trocar 110 is inserted into the port 120 (as shown in FIGS. 1 and 2), the tip 190 of the trocar 110 and the forward tip 180 of the port 120 combine to form a pointed forward tip that is adapted to be inserted through the incision 10 of the patient.

As illustrated in FIG. 2, the intermediate and forward portions 150, 160 include a longitudinally-extending bore 200 therethrough. The bore 200 has a diameter that is sufficiently large to allow insertion of an endo-bag or other surgical instruments therethrough. The bore 200 is preferably between 10 and 14 mm in diameter. An outside diameter of the main portion of the trocar 110 is slightly smaller than the diameter of the bore 200 so that the trocar 110 may be inserted into the port 120.

The overall longitudinal length of the port 120 is preferably about the same as conventional laparoscopic ports/trocars so that conventional surgical instruments may be used with the LSEP 100.

The port 120 may comprise a variety of materials. A disposable port 120 may comprise plastic or PVC. Conversely, a reusable port 120 may comprise steel.

Figure 4:
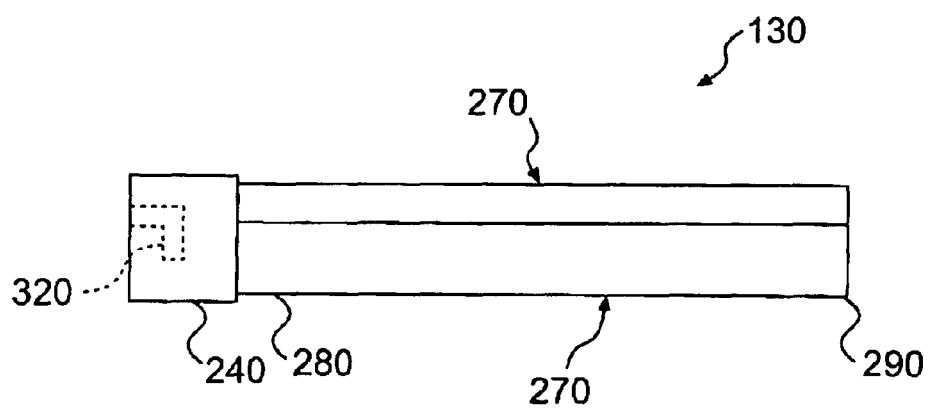
FIG. 4 is a side view of a sheath of the LSEP of FIG. 1.

As illustrated in FIGS. 2 and 4, the sheath 130 includes a holding ring 240 that is manufactured as an integral part of the intermediate portion 150 to allow the holding ring 240 to slide longitudinally (forwardly and rearwardly) on the intermediate portion 150. An inner surface 250 of the holding ring 240 has an inner diameter that is smaller than the largest diameter of the outer surface 170 of the forward portion 160. Consequently, the holding ring cannot slide forwardly relative to the port 120 past the forward portion 160. Similarly, the inner diameter of the holding ring 240 is smaller than the funnel shape of the rearward portion 140 so that the holding ring 240 cannot slide rearwardly past the rearward portion 140. When the LSEP 100 is in the contracted position, the holding ring 240 is longitudinally disposed at a rearward end of the intermediate portion 150.

While the holding ring 240 is shown as an integral portion of the sheath 130, it should be noted that the holding ring 240 may be manufactured as a separate component that is connected to the sheath 130. In such a case, the holding ring 240 may be connected to the sheath 130 in any suitable fashion. For example, the holding ring 240 may be welded, glued, bolted, threadedly affixed, etc. to the sheath 130 without departing from the scope of the present invention.

The sheath 130 includes a plurality of circumferentially-spaced prongs 270 having rearward ends 280 connected to the holding ring 240, either directly or via an intermediate shaft, which increases the length of the sheath 130 relative to the illustrated embodiment. As illustrated in FIG. 2, forward ends 290 of the prongs 270 extend forwardly toward the forward portion 160. The forward ends 290 include forward tips having inside surfaces 300 that taper radially-outwardly as they extend forwardly. Consequently, the inside surfaces 300 of the forward tips of the prongs 270 adjoin the outwardly-tapering outer surface 170 of the forward portion 160 when the LSEP 100 is in the contracted position.

In the illustrated embodiment, three circumferentially-spaced prongs 270 each cover an annular arc of about 120 degrees. It should be noted, however, that the sheath 130 may include a greater or fewer number of prongs 270 without deviating from the scope of the present invention. When the LSEP 100 is in the contracted position, inner surfaces 304 of the prongs 270 generally form a bore that has a diameter that is slightly larger than an outer diameter of the intermediate portion 150. The diameter of the bore is preferably equal to the inside diameter of the holding ring 240 so that the holding ring 240 and prongs 270 form a generally smooth inside bore when in the contracted position.

The inner surfaces 304 of the prongs 270 are smooth so that they do not abrade an endo-bag. Alternatively, the inner surfaces 304 may be textured to help grab an endo-bag as the LSEP 100 extracts a specimen. Alternatively, the inner surface 304 may have a longitudinal ridge or rail that rides in a groove on the outer surface of the intermediate portion 150 of the port 120. The outer surfaces of the prongs 270 are also smooth so that the sheath 130 can more easily slide in and out of an incision 10. The edges of the prongs 270 are preferably at least slightly curved and smoothed so that they do not include any sharp edges that might cut into the patient during surgery.

In the illustrated embodiment, the holding ring 240 and prongs 270 are integrally formed. However, the prongs 270 may alternatively be connected to the holding ring 240 after formation.

As shown in FIG. 2, the holding ring 240 preferably includes an annular indentation 306 at or near the transition between the inner surface 250 of the holding ring 240 and the inner surface 304 of the prongs 270. The annular indentation 306, marks the transition from the holding ring 240 (or, alternatively, an intermediate shaft connected to the holding ring 240) to the prongs 270. The annular indentation 306 facilitates the outward radial movement of the prongs 270 away from the intermediate portion 150 when the LSEP 100 is manipulated into the expanded position. While the annular indentation 306 is shown with a V-shaped cross-section, any other suitable cross-section may be used without deviating from the scope of the present invention. For example, the annular indentation 306 may have a U-shape or a rectangular shape. Regardless of the actual shape employed, the function of the indentation is to facilitate the outward radial expansion of the prongs 270 by providing a folding line.

As would be appreciated by one of ordinary skill in the art, the annular indentation 306 need not be annular to function as a folding line. In an alternate construction, the indentation 306 may comprise a series of indentations that extend around the inner surface 250 of the sheath 130. Still further, the indentation 306 may comprise two or more parallel indentations on the inner surface 250 of the sheath 130. Still further, the indentation 306 may be formed on an outside surface of the sheath 130. In yet another embodiment, where the prongs 270 are sufficiently flexible (either because of the material used or the thickness of the material used), no indentation 306 may be included.

As illustrated in FIG. 2, the holding ring 240 and prongs 270 comprise a strong, flexible material such as plastic or PVC. Consequently, when the LSEP 100 is transitioned from the contracted position into the expanded position, as is discussed in greater detail below, the prongs 270 flex such that the forward ends 290 expand radially-outwardly relative to the rearward ends 280 to form a funnel shape that includes a wedge-shaped gap formed between adjoining prongs 270. Alternatively, the prongs 270 may comprise a stronger, more rigid material such as steel and be hinged at their rearward ends 280 to the holding ring 240, which may also comprise a rigid material such as steel, such that the prongs 270 pivot radially-outwardly when the LSEP 100 is moved into the expanded position. While the material composition of the prongs 270 will dictate the design of their radial thicknesses so that the prongs 270 flex appropriately during expansion of the LSEP 100, as would be appreciated by one of ordinary skill in the art, the radial thickness of the prongs 270 is preferably about 1 or 2 mm.

As an illustrative example, if the port 120 has a 12 mm inside diameter and has a radial thickness of 1 mm and the prongs 270 have a 2 mm radial thickness and flushly adjoin the intermediate portion 150 of the port 120 when in the contracted position, an overall outside diameter of an intermediate portion of the LSEP 100 would be 18 mm.

In the illustrated embodiment, the prongs 270 touch each other when the LSEP 100 is in the contracted position (see FIG. 4). However, the widths of the prongs 270 may be reduced such that, even in the contracted position, there is an longitudinally-extending circumferential gap between adjoining prongs 270. Conversely, the widths of the prongs 270 may also be widened such that adjoining prongs 270 overlap each other like the petals of a rose such that, even when the LSEP 100 is in the expanded position, adjoining prongs 270 touch each other and form a full funnel shape without gaps. (See, e.g., LSEP 500 in FIGS. 17–19.)

If the prongs 270 touch each other when the LSEP 100 is in the contracted position (see FIG. 4), the prongs 270 could be attached to each other by a substance that, if broken off inside the abdominal cavity 40, is absorbed by the patient's body. A derivative of lactic acid may be one such material, since it is readily absorbed by the body. As would be appreciated by those skilled in the art, however, derivatives of lactic acid are not the only substance that may be employed for this purpose. To the contrary, those of ordinary skill in the art would readily recognize that there are a plethora of materials that are absorbable by the body that may be used for this purpose.

The prongs 270 are preferably tinted with a color that is not normally present in the abdominal cavity 40 of a patient. Possible colors include orange, bright green, etc. Such coloring aids the surgeon in seeing the prongs 270. Additionally, the inside surfaces 304 and outside surfaces of the prongs 270 may be colored differently to help the surgeon know what side of each prong 270 he/she is looking at. If the prongs 270 are colored to be distinguishable from tissue, the prongs 270 are also easily identifiable if one or more of the prongs 270 should accidentally separate from the holding ring 240 during surgery. This greatly facilitates identification and removal from the patient. Alternatively, the prongs 270 may be made from (or incorporate) a radio-opaque material. If made from a radio-opaque material (or if incorporating a radio-opaque material at least in part therein), the prongs 270 may be easily located by illumination with x-rays. Therefore, if one of the prongs 270 should be disengaged from the holding ring 240, it may be more easily located.

Figure 5:
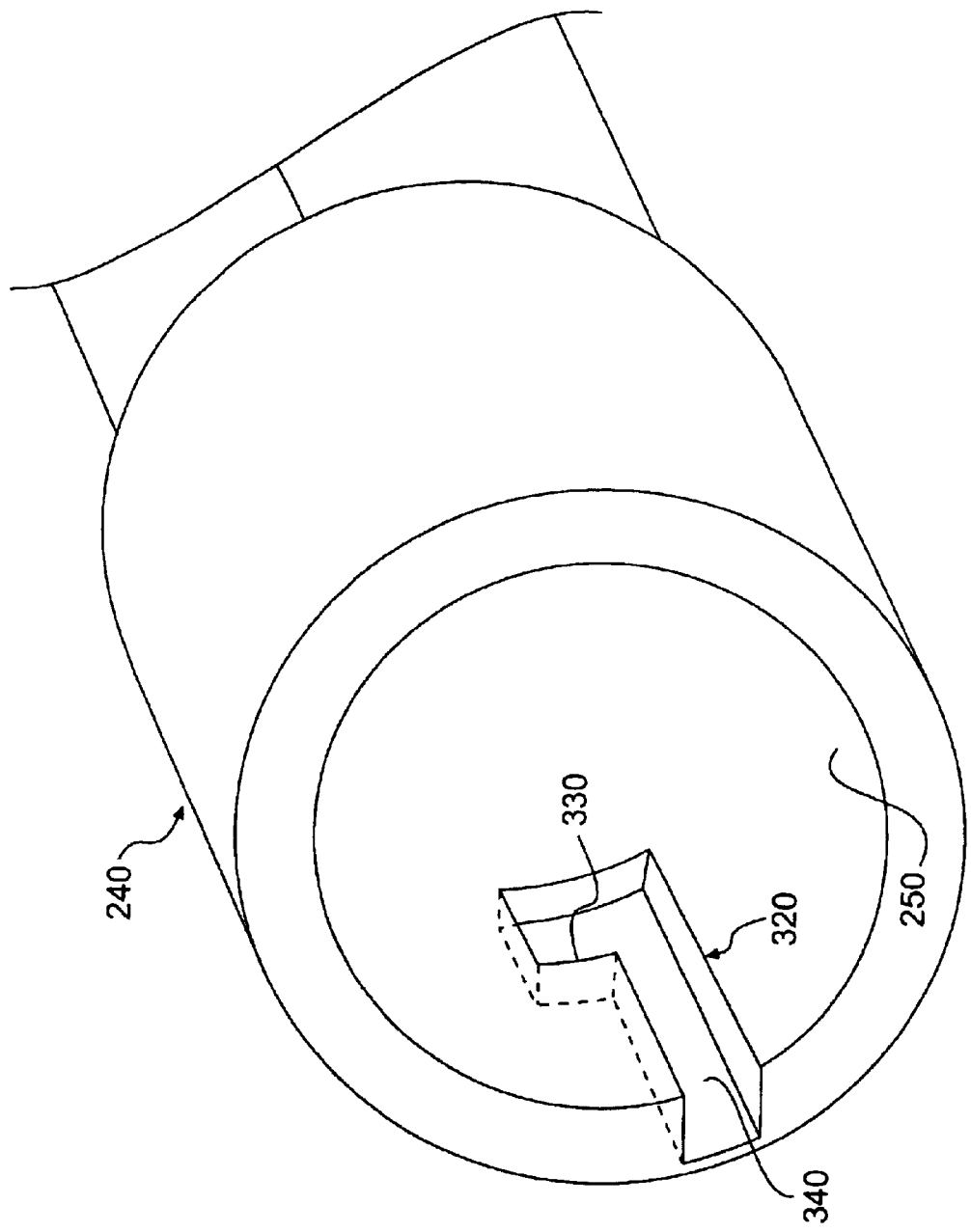
FIG. 5 is a partial perspective view of the sheath of the LSEP of FIG. 1, as viewed from the rearward side of the sheath.

As illustrated in FIG. 2, a releasable holding mechanism 310 selectively secures the holding ring 240 at the rear end of the intermediate portion 150 when the LSEP 100 is in the contracted position. As illustrated in FIGS. 4 and 5, the holding mechanism 310 includes an L-shaped groove 320 on the inner surface 250 of the holding ring 240. A forwardly-facing surface 330 is defined on one circumferentially-extending leg of the groove 320. The other leg of the groove 320 extends rearwardly from the first leg to the rearward end of the holding ring 240 and defines a rearwardly-extending notch 340. As illustrated in FIGS. 2 and 3, the holding mechanism 310 also includes a protrusion 350 extending radially-outwardly from the outer surface of a rearward portion of the intermediate portion 150. As illustrated in FIG. 2, when the LSEP 100 is in the contracted position, a rearward edge of the protrusion 350 is positioned in front of the forwardly-facing surface 330. Consequently, the holding mechanism 310 prevents the holding ring 240 from sliding forwardly relative to the port 120 when the LSEP is in the contracted position. To extend the LSEP 100 into the expanded position, the surgeon rotates the port 120 (counterclockwise as viewed from the rear end of the LSEP 100 in the illustrated embodiment) relative to the holding ring 240 until the protrusion 350 aligns with the notch 340. The protrusion 350 can thereafter move through the notch 340 and the port 120 can move rearwardly relative to the holding ring 240 to permit the surgeon to manipulate the LSEP 100 into the expanded position.

While only one is illustrated in FIGS. 4 and 5, the holding mechanism 310 may include a plurality of mating sets of protrusions 350 and L-shaped grooves 320, as would be appreciated by one of ordinary skill in the art.

The holding mechanism 310 may also include a safety device that tends to prevent the holding mechanism 310 from accidentally releasing. Such a safety device may function in the same manner as safety caps for medicine bottles. Alternatively, the safety device may include a break-away ring like the rings used on milk jugs to prevent the port 120 from rotating relative to the holding ring 340 until a sufficient torque is supplied.

While in the illustrated embodiment, the holding mechanism 310 comprises a protrusion 350 and mating groove 340, the holding mechanism 310 may comprise a variety of other types of mechanisms without deviating from the scope of the present invention. For example, the holding mechanism 310 may alternatively comprise a threaded portion on the holding ring 240 and a mating threaded portion on the intermediate portion 150 such that the surgeon releases the holding mechanism 310 by unscrewing the port 120 from the holding ring 240.

In the illustrated embodiment, the cross-sections of the port 120 and sheath 130 are circular. However, the present invention is not so limited. Other cross-sections such as ovoid shapes may also be used. Nonetheless, circular cross-sections are preferred because they include smooth curves and provide the largest cross-sectional area for the bore 200 relative to an outer perimeter (and therefore incision 10 size) of the sheath 130. In addition, a circular cross-section facilitates rotational movement of the sheath 130 relative to the port 120.

The operation of the LSEP 100 is described with sequential reference to FIGS. 6–10. To use the LSEP 100, the surgeon first inserts the contracted LSEP 100 and trocar 110 into an incision 10 in the abdominal wall 20 of the patient. The surgeon then removes the trocar 110 and can use the port 120 with conventional surgical instruments. During such use, the sheath 130 is disposed between the port 120 and the incision 10. As may be appreciated from FIG. 6, the trocar 110 has been removed.

Figure 6:
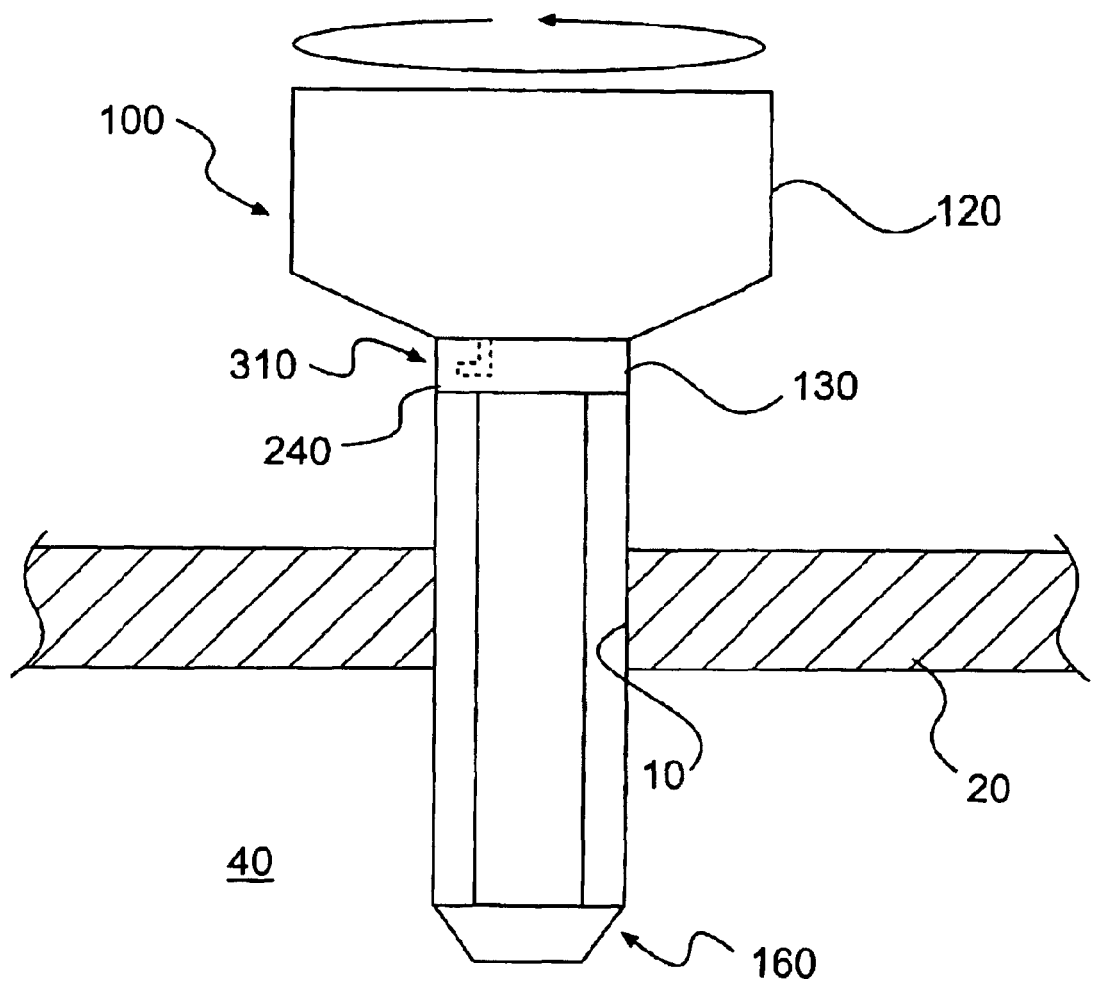
FIGS. 6–10 are side views showing the sequential operation of the LSEP of FIG. 1.

As illustrated in FIG. 6, when the surgeon uses the LSEP 100 to extract a specimen 50, the surgeon first rotates the port 120 relative to the sheath 130 to release the holding mechanism 310.

Figure 7:
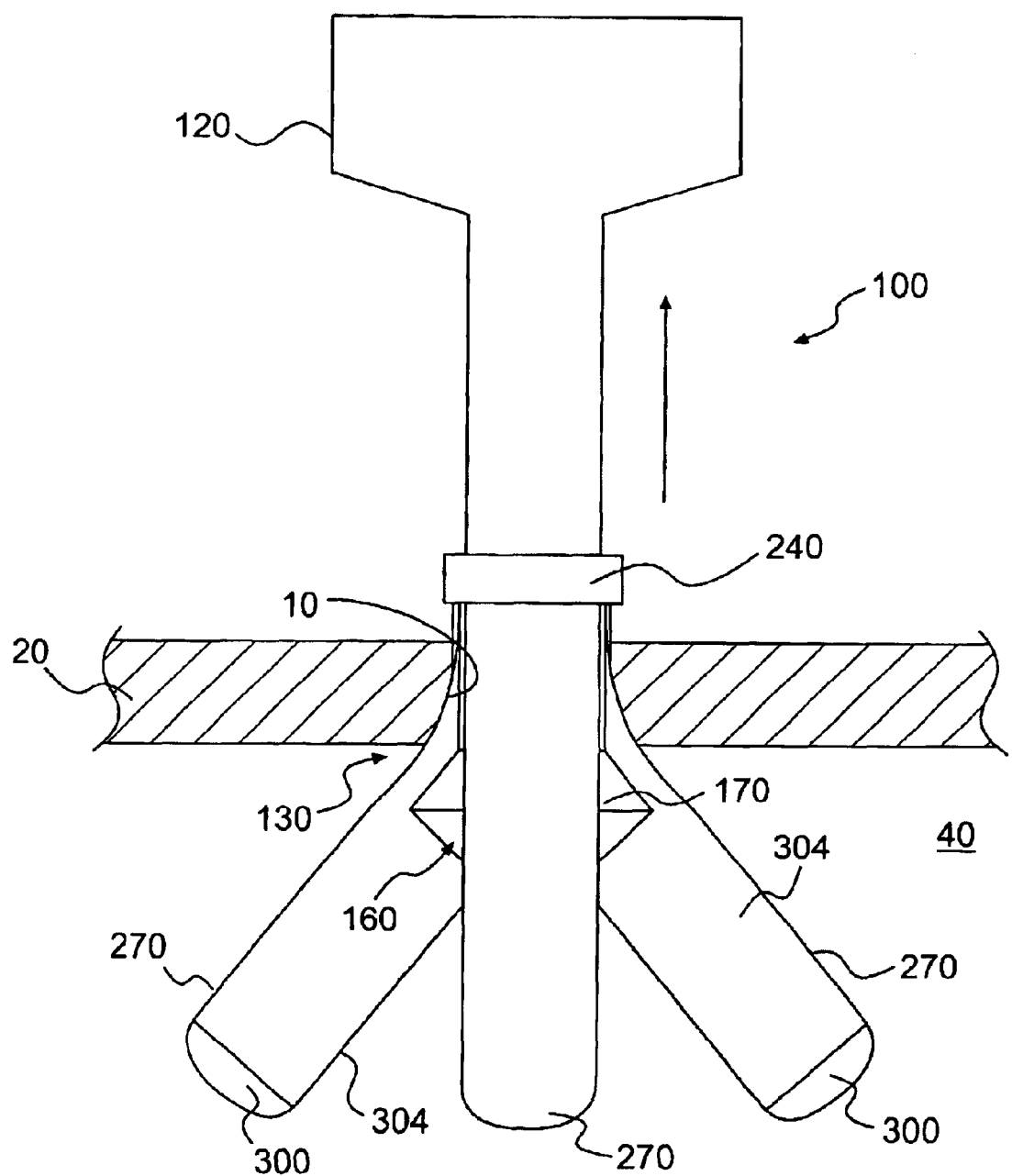
Figure 8:
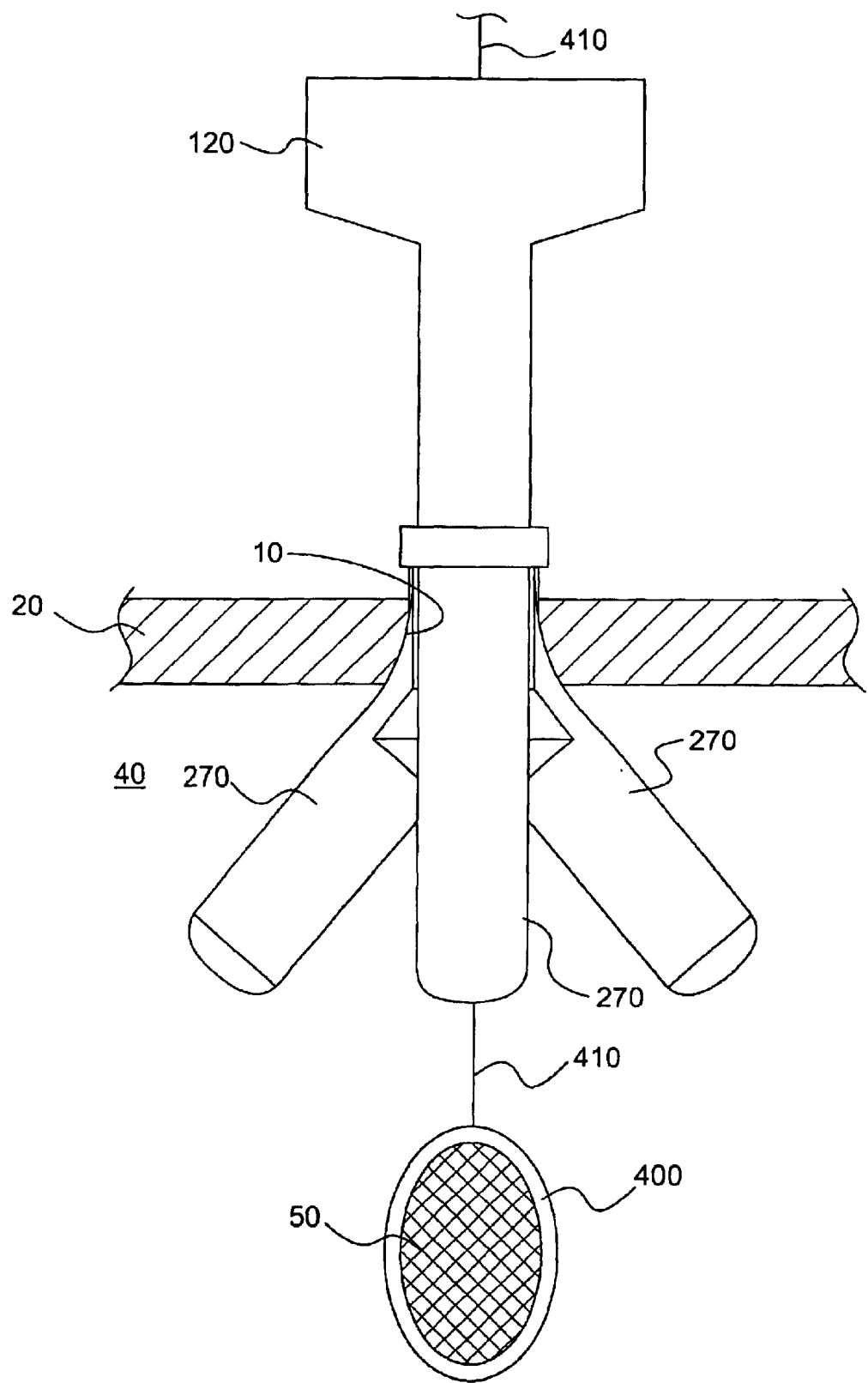

As illustrated in FIG. 7, the surgeon next uses one of his/her hands to hold the holding ring 240 stationary relative to the patient and uses his/her other hand to slide the port 120 rearwardly (in the direction of the arrow) relative to the holding ring 240. As the forward portion 160 slides rearwardly relative to the prongs 270, the tapered outer surface 170 of the forward portion slidingly engages the inside surfaces 300 of the forward ends 290 of the prongs 270, thereby forcing the forward ends of the prongs 270 to flex radially-outwardly. Thereafter, the outer surface 170 of the forward portion 160 of the port 120 engages inner surfaces 304 of the prongs 270, further expanding the prongs 270 as the LSEP 100 transitions into increasingly expanded positions. When the forward portion 160 approaches the holding ring 240, the port 120 cannot slide further rearwardly relative to the holding ring 240 because the inside diameter of the holding ring 240 and the rearward ends 280 of the prongs 270 are smaller than the outer diameter of the forward portion 160. FIG. 8 illustrates the fully expanded position of the LSEP 100.

As illustrated in FIG. 8, the surgeon then inserts an endo-bag 400 into the abdominal cavity 40 through the port 120. It should be noted that the endo-bag 400 is usually inserted into the abdominal cavity 40 before the LSEP 100 is manipulated into the expanded position. The surgeon then places the specimen 50 into the endo-bag 400 using a conventional technique.

Like the endo-bag 60, the endo-bag 400 includes a purse string 410 closing mechanism. It is believed that the endo-bag 400 to be used with the LSEP 100 will have to be longer (i.e., larger) than endo-bags 60 used in the prior art. In prior art endo-bags 60, the surgeon often pulled a portion of the endo-bag 60 out from the top of the port 30 prior to extraction of the port 30 and endo-bag 60 from the patient. The surgeon typically would grasp the top of the endo-bag 60 during removal of the specimen 50 from the patient. To provide the same operation with the LSEP 100, the endo-bag 400 will probably be longer than the conventional endo-bag 60 because it will have to extend through both the port 120 and sheath 130 when in the expanded position.

Figure 9:
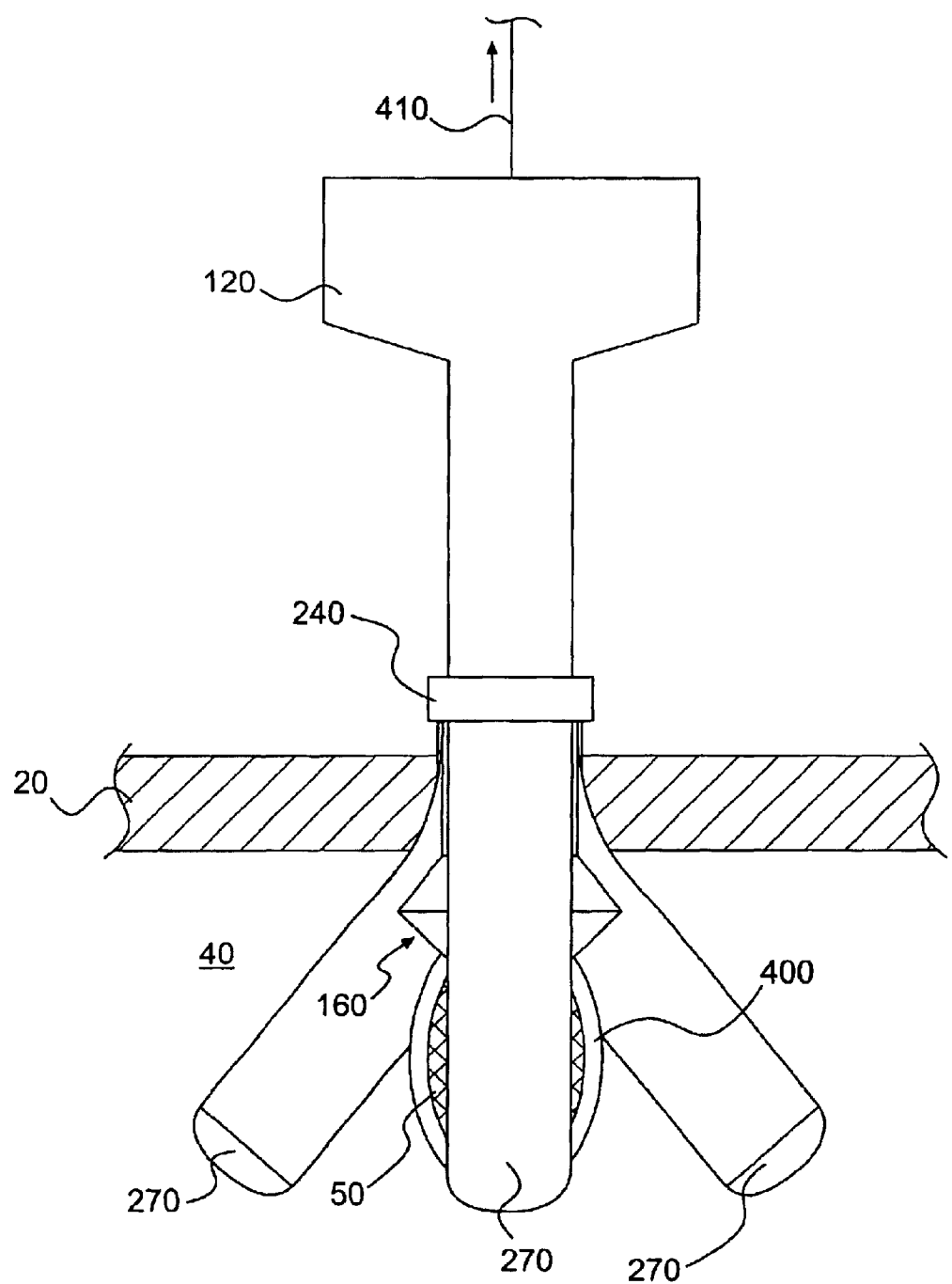

As illustrated in FIG. 9, after placing the specimen 50 into the endo-bag 400, the surgeon pulls the purse string 410 in the direction of the arrow at the rearward end of the port 120. Pulling the purse string 410 closes the endo-bag 400 and moves the endo-bag 400 and specimen 50 toward and into the funnel shape formed by the expanded prongs 270 of the LSEP 100 in the expanded position.

Figure 10:
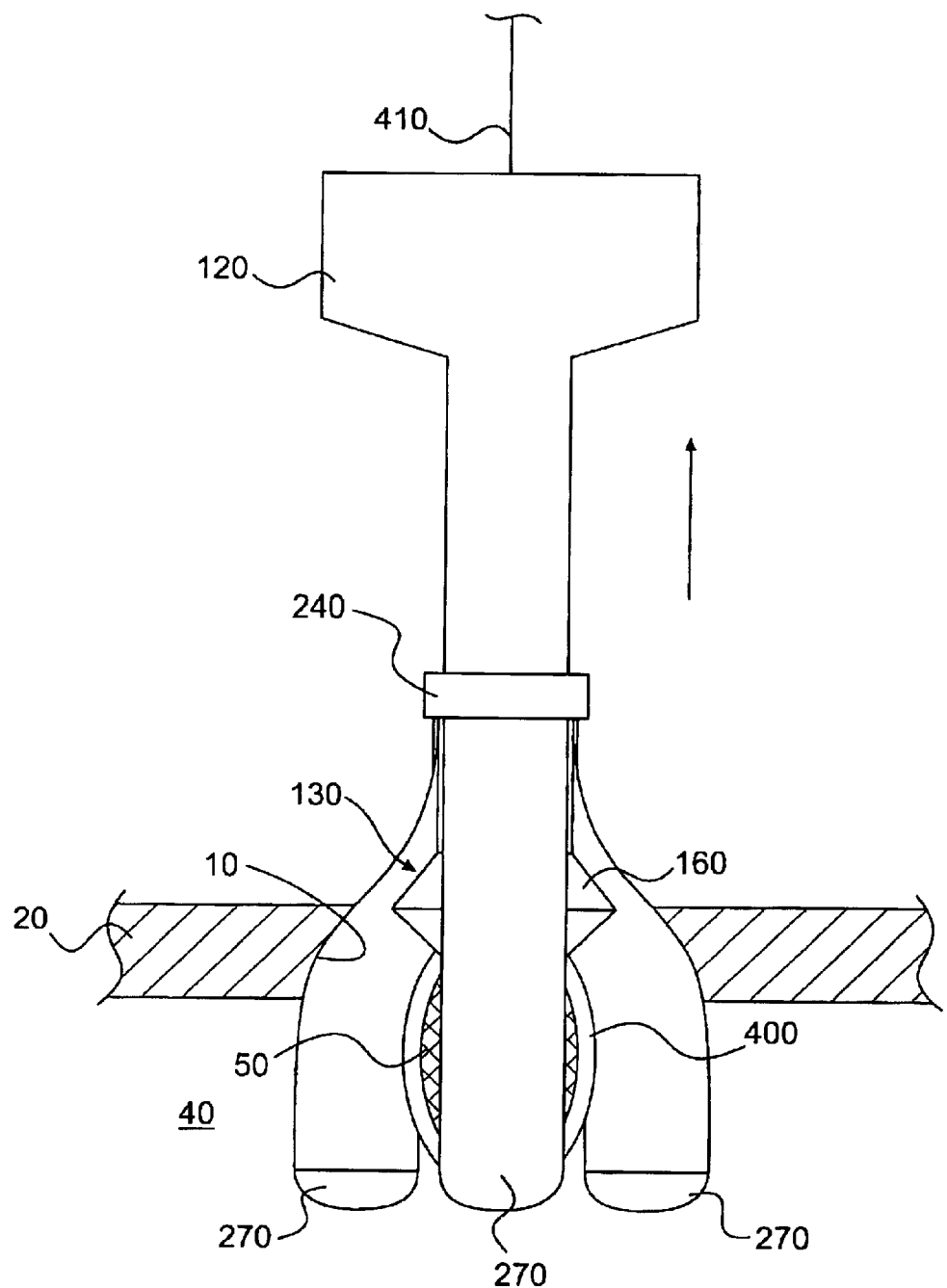

As illustrated in FIG. 10, the surgeon then simultaneously pulls on the purse string 410 and the port 120 in the direction of the arrow to extract the sheath 130, endo-bag 400, and specimen 50 through the incision 10. Because the abdominal wall 20 includes a tough, fibrous layer of fascia, the incision 10 resists expansion as the prongs 270, endo-bag 400, and specimen 50 are extracted. As a result, the prongs 270 contract radially-inwardly under the contracting force of the incision 10, which, in turn, causes the prongs 270, in combination with the elongated endo-bag 400, to manipulate the specimen 50 into an elongated, narrow shape that approximates the inside bore shape of the contracted sheath 130 and more easily squeezes through the incision 10. The smooth outer surfaces of the prongs 270 act like shoe horns for the specimen 50 and endo-bag 400 to further facilitate extraction of the specimen 50 through the incision 10. Consequently, the surgeon can extract the specimen 50 and endo-bag 400 from the abdominal cavity 40 through the incision 10 without having the specimen 50 bunch up in the endo-bag 400, as is disadvantageously the case with conventional extraction techniques.

The LSEP 100 of the present invention enables a surgeon to extract a specimen 50 using less force than conventional techniques and without having to enlarge the incision 10. The LSEP 100 advantageously prevents the specimen 50 from bunching in the endo-bag 400 and causing further complications during surgery. The LSEP 100 also minimizes the risk of rupturing the specimen 50 or endo-bag 400 and reduces the risk of spreading infectious, bilious, and/or cancerous material into the incision 10 or the patient's abdominal cavity.

Various features of the LSEP 100 of the present invention have been exaggerated in the figures to more clearly illustrate their structure. For example, the diameter of the forward portion 160 has been exaggerated in order to clearly illustrate the outer surface 170 and how the forward portion 160 interacts with the prongs 270. The figures are provided for illustrative purposes only and do not illustrate the precise relative dimensions of the components of the LSEP 100.

Figure 17:
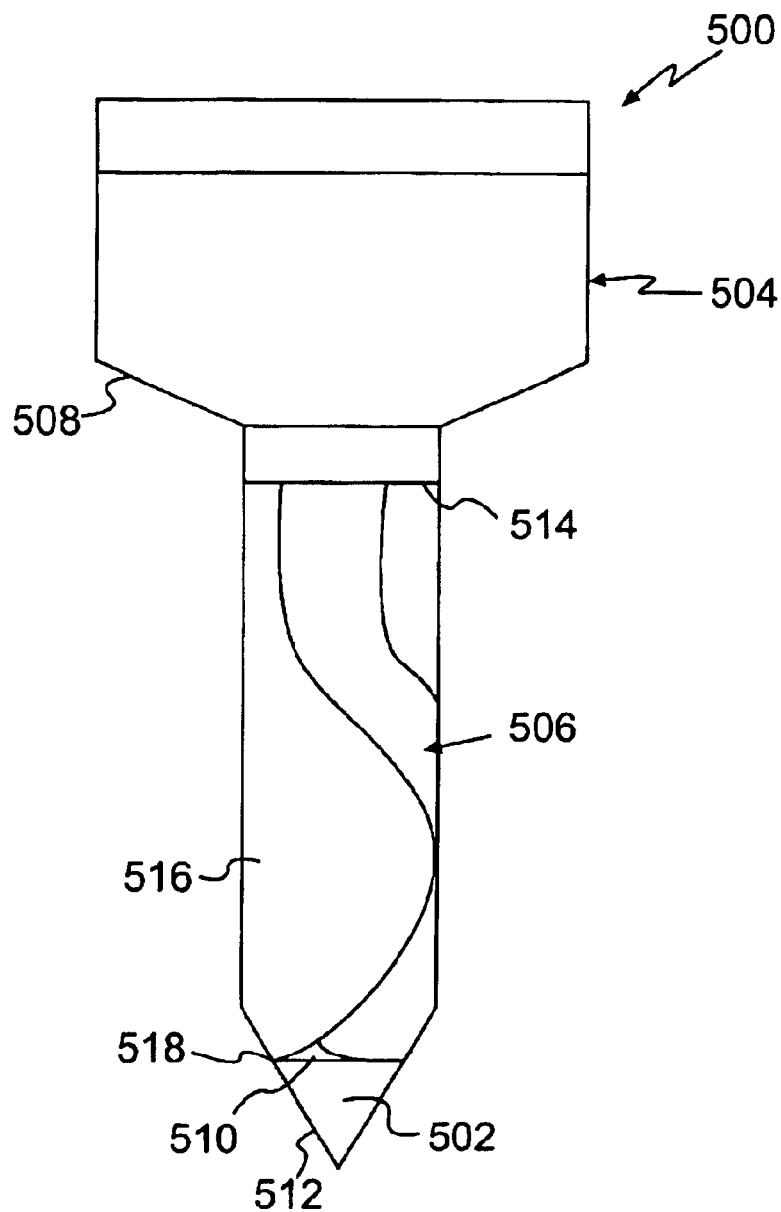
FIG. 17 is a side view of an LSEP according to another embodiment of the present invention.

FIG. 17 illustrates another embodiment of an LSEP 500 according to the teachings of the present invention. Like the LSEP 100, the LSEP 500 includes a pointed trocar 502, a port 504, and a sheath 506. The LSEP 500 also has expended and contracted positions.

The construction of the LSEP 500 is similar to the LSEP 100. To facilitate an understanding of the LSEP 500 without repeating a discussion of all of the details of the LSEP 100, the following discussion of the LSEP 500 focuses primarily on the elements of the LSEP 500 that differ from the LSEP 100. In addition, during surgery, the LSEP 500 is used in the same manner as the LSEP 100. Accordingly, the discussion of the LSEP 100 applies to the LSEP 500.

The port 504 is generally funnel-shaped and tapers radially-inwardly toward an intermediate portion, like the LSEP 100. A flapper valve (not shown) like the conventional flapper valve 45 illustrated in FIGS. 15 and 16 is preferably disposed in the rearward portion 508 to preserve pneumoperitoneum during surgery when surgical instruments are not inserted through the port 504. The intermediate portion is longitudinally elongated and preferably has a constant cross-section over its longitudinal length.

A forward (or distal) portion 510 of the port 504 extends forwardly from the intermediate portion and is radially-enlarged relative to the intermediate portion. The forward portion 510 includes an outer surface that tapers radially-outwardly from a forward end of the intermediate portion. The outer surface is preferably frustroconical, as in the LSEP 100. The forward portion 510 also includes a forward tip that tapers radially-inwardly from the forward edge of the outer surface. The inward taper of the forward tip preferably matches an inward taper of an inwardly-tapering tip 512 of the trocar 502 such that when the trocar 502 is inserted into the port 504, the tip 512 of the trocar 502 and the forward tip of the port 504 combine to form a pointed forward tip that is adapted to be inserted through the incision 10 of the patient.

As with the LSEP 100 illustrated in cross-section in FIG. 2, the intermediate and forward portions 510 include a longitudinally-extending bore therethrough. The bore has a diameter that is sufficiently large to allow insertion of an endo-bag 522 or other surgical instruments therethrough. The bore is preferably between 10 and 14 mm in diameter. An outside diameter of the main portion of the trocar 502 is slightly smaller than the diameter of the bore so that the trocar 502 can be inserted into the port 504. The overall longitudinal length of the port 504 is preferably about the same as conventional laparoscopic ports/trocars so that conventional surgical instruments can be used with the LSEP 500.

The sheath 506 includes a holding ring 514 that is manufactured as an integral part of the intermediate portion to allow the holding ring 514 to slide longitudinally (forwardly and rearwardly) on the intermediate portion. The construction of the holding ring 514 is similar to that of the holding ring 240 of LSEP 100 and, as a result, will not be repeated here.

The sheath 506 of the LSEP 500 includes a plurality of circumferentially-spaced prongs 516 connected to the holding ring 514, either directly or via an intermediate shaft, which extends the length of the sheath 506. Forward ends 518 of the prongs 516 extend forwardly toward the forward portion 510. The forward ends 518 include forward tips having inside surfaces that taper radially-outwardly as they extend forwardly. Consequently, the inside surfaces of the forward tips of the prongs 516 adjoin the outwardly-tapering outer surface of the forward portion 510 when the LSEP 500 is in the contracted position.

In the illustrated embodiment, three circumferentially-spaced prongs 516 each cover an annular arc of about 120 degrees at the portions adjacent to the ring 514. It should be noted, however, that the sheath 506 may include a greater or fewer number of prongs 516 without deviating from the scope of the present invention.

When the LSEP 500 is in the contracted position, inner surfaces of the prongs 516 generally form a bore that has a diameter that is slightly larger than an outer diameter of the intermediate portion. The diameter of the bore is preferably equal to the inside diameter of the holding ring 514 so that the holding ring 514 and prongs 516 form a generally smooth inside bore when in the contracted position.

In the illustrated embodiment, the holding ring 514 and prongs 516 are integrally formed. However, the prongs 516 may alternatively be connected to the holding ring 514 via a suitable connection such as an ultrasonic weld, or some other fastening method or structure known to those skilled in the art.

As with the LSEP 100, the holding ring 514 preferably includes an annular indentation at or near the transition between the inner surface of the holding ring 514 and the inner surface of the prongs 516. Alternatively, where an intermediate shaft connects the holding ring 514 to the prongs 516, the annular indentation is positioned at the rearward ends of the prongs 516. In the embodiment illustrated, the annular indentation marks the transition from the holding ring 514 to the prongs 516. The annular indentation facilitates the outward radial movement of the prongs 516 away from the intermediate portion when the LSEP 500 is manipulated into the expanded position.

The holding ring 514 and prongs 516 preferably comprise a strong, flexible material such as plastic or PVC. Consequently, when the LSEP 500 is transitioned from the contracted position into the expanded position, the prongs 516 flex such that the forward ends 518 expand radially-outwardly to form a funnel shape. While the material composition of the prongs 516 will dictate the design of their radial thickness so that the prongs 516 flex appropriately during expansion of the LSEP 500, as would be appreciated by one of ordinary skill in the art, the radial thickness of the prongs 516 is preferably about 1 or 2 mm.

Figure 18:
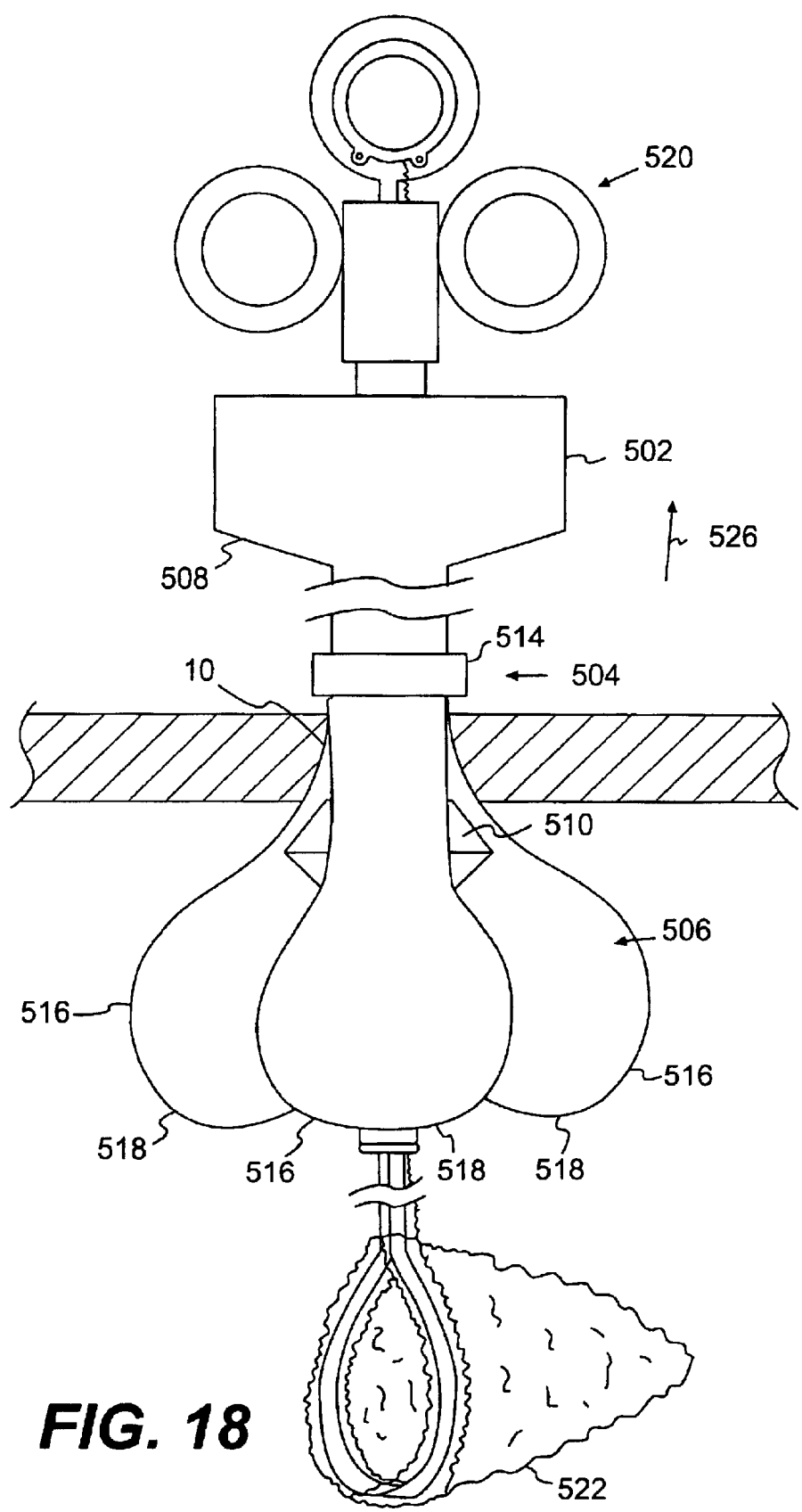
FIG. 18 is a side view of the LSEP illustrated in FIG. 17, showing a prior art endoscopic retrieval bag device disposed therein prior to synching of the purse string connected to the bag.
Figure 19:
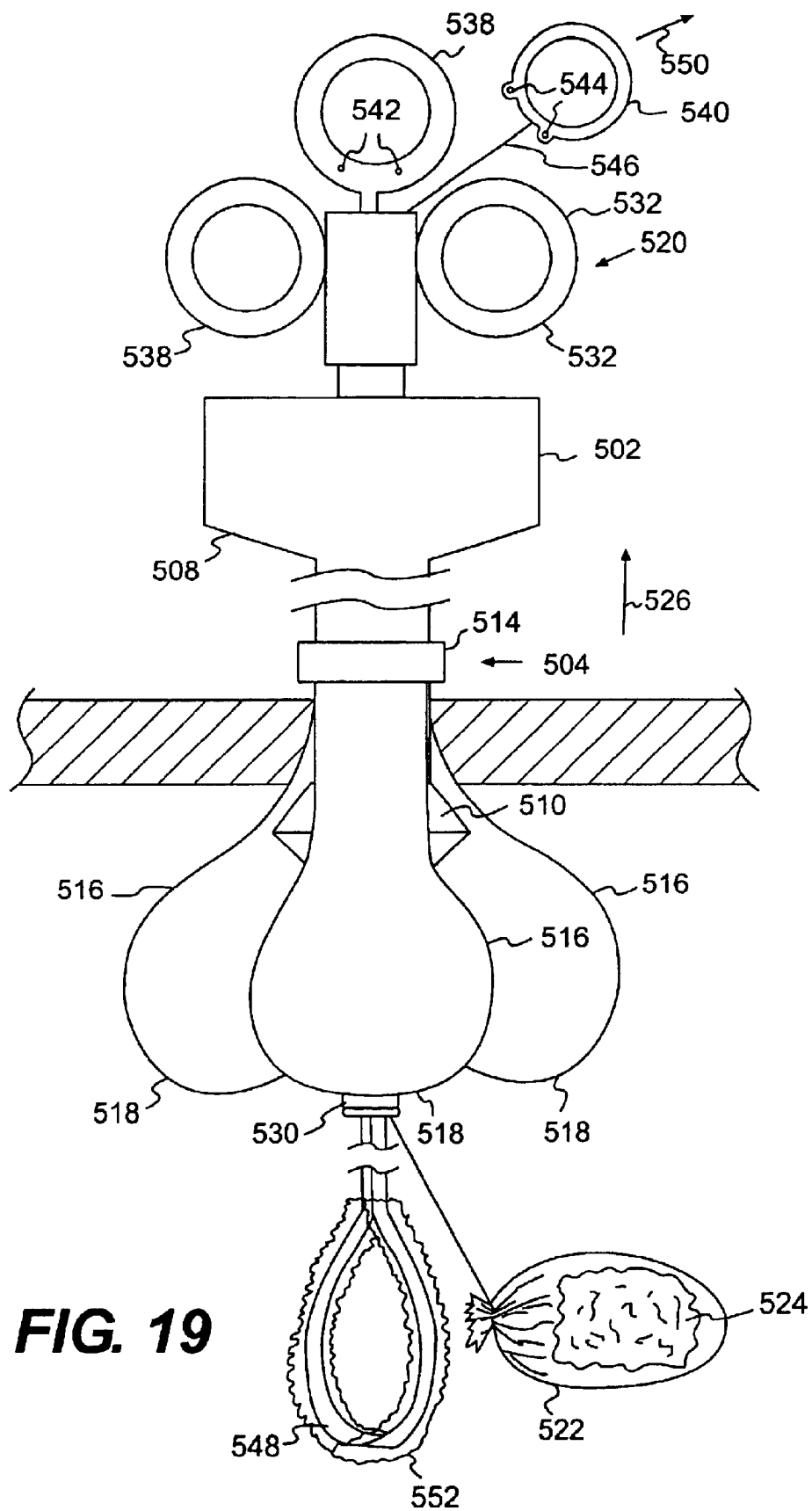
FIG. 19 is a side view of the LSEP depicted in FIG. 18, shown after the bag has been synched, but prior to removal of a specimen from a patient.

As illustrated in FIGS. 17–19, the prongs 516 are shoehorn-shaped such that they extend laterally outward as the extend from the holding ring 514 to their forward ends 518. As shown, the prongs 516 are wider at their forward ends 518 that at the ends attached to the holding ring 514.

FIG. 17 illustrates the LSEP 500 when in the contracted position. As shown, the prongs 516 partially overlap one another near their forward ends 518. When the LSEP 500 is opened to the extended position, as shown in FIGS. 18 and 19, the prongs expand laterally outward so that they are no longer in an overlapping condition. As would be appreciated by those skilled in the art, the extent to which the LSEP 500 has been transitioned into the expanded condition will establish the extent to which there is overlap between the prongs 516. in use, the prongs 516 are designed to establish essentially a funnel shape when in the expanded position.

The prongs 516 illustrated in FIGS. 18 and 19 are shown with a shoehorn shape. As would be appreciated by those skilled in the art, however, the present invention encompasses an infinite variety of shapes for the prongs 516 and need not be the shoehorn shape depicted. Specifically, the LSEP 500 may be constructed with prongs 516 with any flared shape including a triangular shape, a rectangular shape, a polygonal shape, an ellipsoidal shape, an oval shape, or the like.

As with LSEP 100, the prongs preferably are made of a plastic material. In the illustrated embodiment, the prongs are formed as a part of the ring 514. As would be appreciated by those skilled in the art, however, the prongs 516 may be constructed of any suitable material and need not be made of plastic. Instead, for example, the prongs 516 could be made of a metal material that is hingedly attached to the ring 514.

As with LSEP 100, the port 504 preferably has a 12 mm inside diameter and has a radial thickness of 1 mm and the prongs 514 have a 2 mm radial thickness and flushly adjoin the intermediate portion of the port 504 when in the contracted position. As a result, an overall outside diameter of an intermediate portion of the LSEP 100 would be about 18 mm.

The prongs 514 are preferably tinted with a color that is not normally present in the abdominal cavity 40 of a patient. Possible colors include orange, bright green, etc. Such coloring aids the surgeon in seeing the prongs 516. Additionally, the inside surfaces and outside surfaces of the prongs 516 may be colored differently to help the surgeon know what side of each prong 516 he/she is looking at. If the prongs 516 are colored to be distinguishable from tissue, the prongs 516 are also easily identifiable if one or more of the prongs 516 should accidentally separate from the holding ring 514 during surgery. This greatly facilitates identification and removal from the patient. Alternatively, the prongs 516 may be made from (or incorporate) a radio-opaque material. If made from a radio-opaque material (or if incorporating a radio-opaque material at least in part therein), the prongs 516 may be easily located by illumination with x-rays Therefore, if one of the prongs 516 should be disengaged from the holding ring 514, it may be more easily located.

As illustrated in FIG. 2, a releasable holding mechanism may selectively secure the holding ring 514 at the rear end of the intermediate portion when the LSEP 500 is in the contracted position. The holding mechanism for the LSEP 500 is contemplated to be the same as the holding mechanism 310 illustrated in connection with LSEP 100. As a result, the holding mechanism will not be further detailed in connection with the LSEP 500.

In the illustrated embodiment, the cross-sections of the port 504 and sheath 506 are circular. However, the present invention is not so limited. Other cross-sections such as ovoid shapes may also be used. Nonetheless, circular cross-sections are preferred because they include smooth curves and provide the largest cross-sectional area for the bore relative to an outer perimeter (and therefore incision 10 size) of the sheath 506. In addition, a circular cross-section facilitates rotational movement of the sheath 506 relative to the port 504.

The operation of the LSEP 500 is the same as that described in connection with the LSEP 100 and illustrated with reference to FIGS. 6–10. Accordingly, no further description is provided with respect to the operation of the LSEP 500, except as detailed below.

After removal of the trocar 502, the surgeon may insert an endoscopic retrieval bag device ("ERBD") 520 through the port 504. The details of the ERBD 520 will be discussed below in connection with FIGS. 20 and 21. The ERBD 520 is a self-contained device designed to deploy a specimen bag 522 with the patient so that a specimen 524 may be inserted thereinto for removal from the patient as illustrated in FIG. 19.

When the surgeon uses the LSEP 500 to extract a specimen 524, the surgeon first rotates the port 504 relative to the sheath 506 to release the holding mechanism 310. The surgeon then holds the holding ring 514 stationary relative to the patient with one hand and uses his/her other hand to slide the port 504 rearwardly (in the direction of the arrow 526) relative to the holding ring 514. As the forward portion slides rearwardly relative to the prongs 516, the tapered outer surface of the forward portion 510 slidingly engages the inside surfaces of the forward ends 518 of the prongs 516, thereby forcing the forward ends of the prongs 516 to flex radially-outwardly. Thereafter, the outer surface of the forward portion 510 of the port 504 engages inner surfaces of the prongs 516, further expanding the prongs 516 as the LSEP 500 transitions into increasingly expanded positions. When the forward portion 510 approaches the holding ring 514, the port 504 cannot slide further rearwardly relative to the holding ring 514 because the inside diameter of the holding ring 514 and the rearward ends of the prongs 516 are smaller than the outer diameter of the forward portion 510. As illustrated in FIGS. 18 and 19, the surgeon then inserts the ERBD 520 into the abdominal cavity 40 through the port 504.

Figure 20:
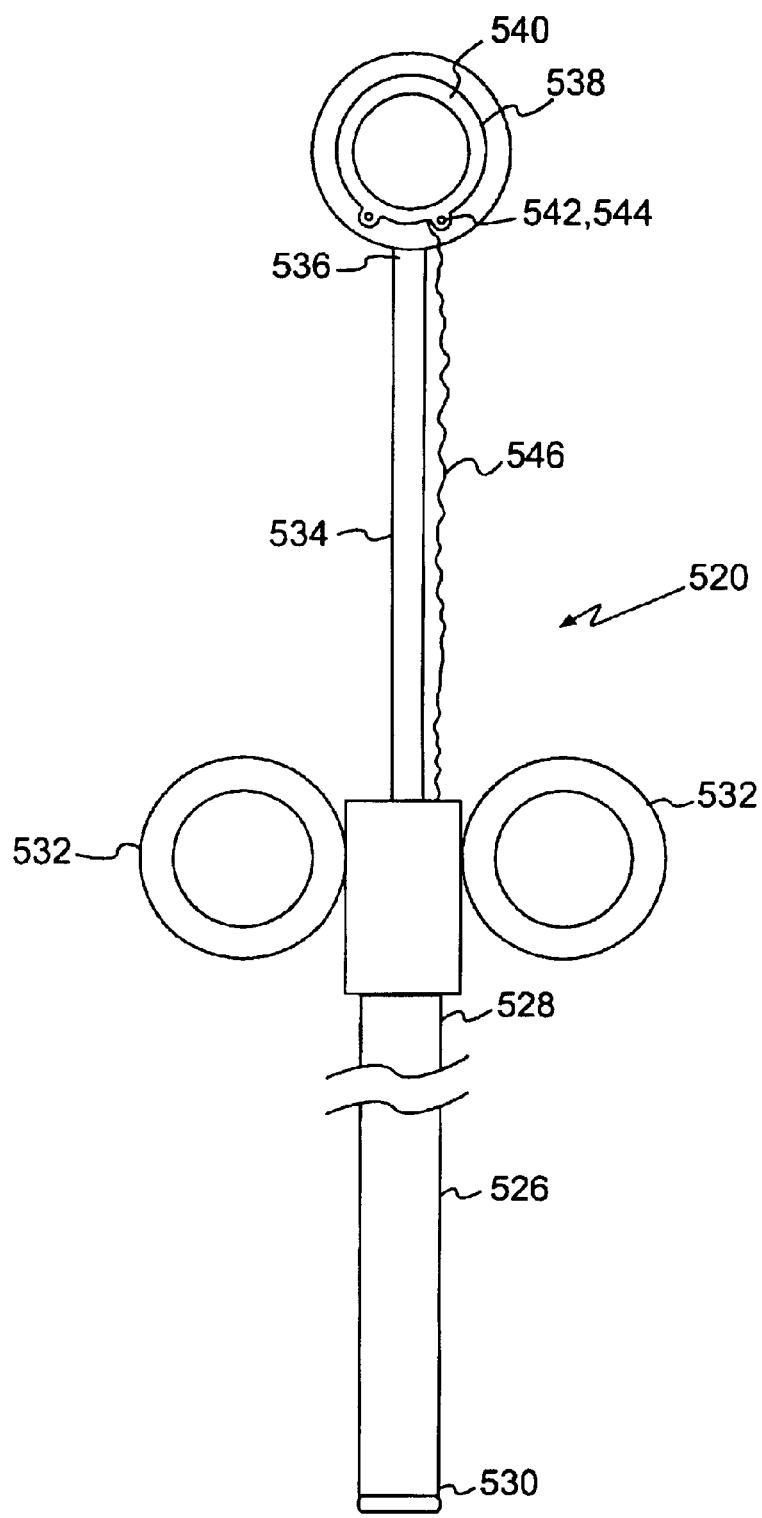
FIG. 20 is a side view of the prior art endoscopic retrieval bag device illustrated in combination with the LSEP shown in FIGS. 18 and 19, shown in a pre-deployed state.
Figure 21:
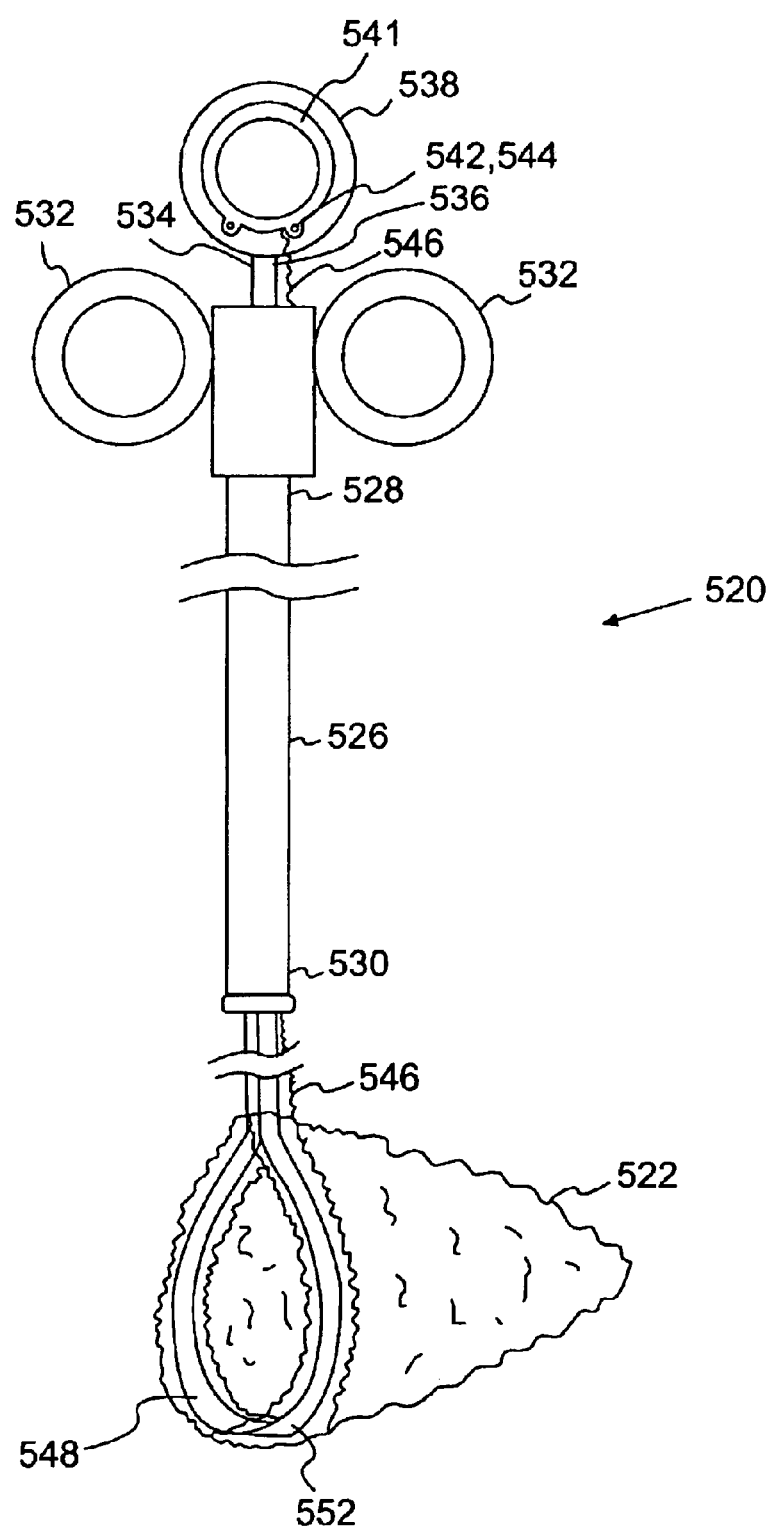
FIG. 21 is a side view of the prior art endoscopic retrieval bag device illustrated in FIG. 20, shown in a deployed state.

The construction of the ERBD 520 is illustrated in FIGS. 20 and 21. FIG. 20 illustrates the ERBD 520 in a non-deployed condition. FIG. 21 illustrates the ERBD 520 in a deployed condition.

As shown in FIGS. 20 and 21, the ERBD has a primary shaft 526 with a proximal end 528 and a distal end 530. Two finger holds 532 are connected to the proximal end 528 of the primary shaft 526 to accommodate the surgeon's fingers. A secondary shaft 534 is disposed slidingly within the primary shaft 526. The secondary shaft 534 has a proximal end 536 with a finger hold 538 disposed thereon. A finger loop 540 is removably attached to the finger hold 538 preferably by one or more posts 542 that engage holes 544 in the finger loop 540. A purse string 546 is connected to the finger loop 540 and extends to the specimen bag 522.

In the non-deployed condition, the specimen bag 522 is disposed within the distal end ERBD 520 preferably in a folded condition. After inserting the ERBD 520 into the patient, the surgeon pushes on the finger hold 538 to slide the secondary shaft 534 into the primary shaft 526. A flat wire 548 is attached to the distal end of the secondary shaft 534. The flat wire 548 is preconditioned to expand into a loop when pushed out of the distal end 530 of the primary shaft 526. Since the specimen bag 522 is disposed on the flat wire 546, the specimen bag 522 deploys once the specimen bag 522 has been forced out of the distal end 530 of the primary shaft 526 by operation of the secondary shaft 534.

Once a specimen 524 has been placed in the specimen bag 522, as illustrated in FIG. 19, the surgeon separates the finger loop 540 from the finger hold 538 and pulls on the purse string 546 in the direction of arrow 550. Since the purse string 546 is incorporated into the specimen bag 522, the purse string 546 separates the specimen bag 522 from the flat wire 548, leaving a waste portion 552 retained on the flat wire 548. As the purse string 546 is pulled further away from the finger hold 538, the purse string cinches around the specimen 524 so that the specimen 524 may be removed from the patient through the incision 10.

As suggested above, the flat wire 548 preferably is made of a metallic material with sufficient rigidity to expand when pushed out of the distal end 530 of the primary shaft 526 and deploy the specimen bag 522. Of course, the flat wire 548 could be made of any suitable material including plastic. Alternatively, the flat wire 548 may be a wire with a circular, elliptical, or ovoid construction, as would be appreciated by those skilled in the art.

The waste portion 552 of the specimen bag 522 is securely fastened to or around the flat wire 548 so that the waste portion 552 does not become dislodged when the specimen bag 522 is separated therefrom. To facilitate separation of the specimen bag 522 from the waste portion 552, the specimen bag 522 may be perforated at a location intermediate to the flat wire 548 and the purse string 546. So that the purse string 546 may cinch the specimen bag 522 when pulled, the purse string 546 may be woven into the specimen bag 522 or incorporated between two layers thereof.

Once the specimen 524 has been cinched within the specimen bag 522, the surgeon pulls the purse string 546 in the direction of the arrow 550, thereby pulling the specimen bag 522 toward the distal end 530 of the ERBD 520. The ERBD 520, the specimen bag 522, and the port 540 are removed together from the patient. During extraction, the prongs 516 close around the specimen bag 522 to facilitate removal of the specimen 524 from the patient. The prongs 516 discourage rupture of the specimen bag 522, just as with the LSEP 100.

Figure 26:
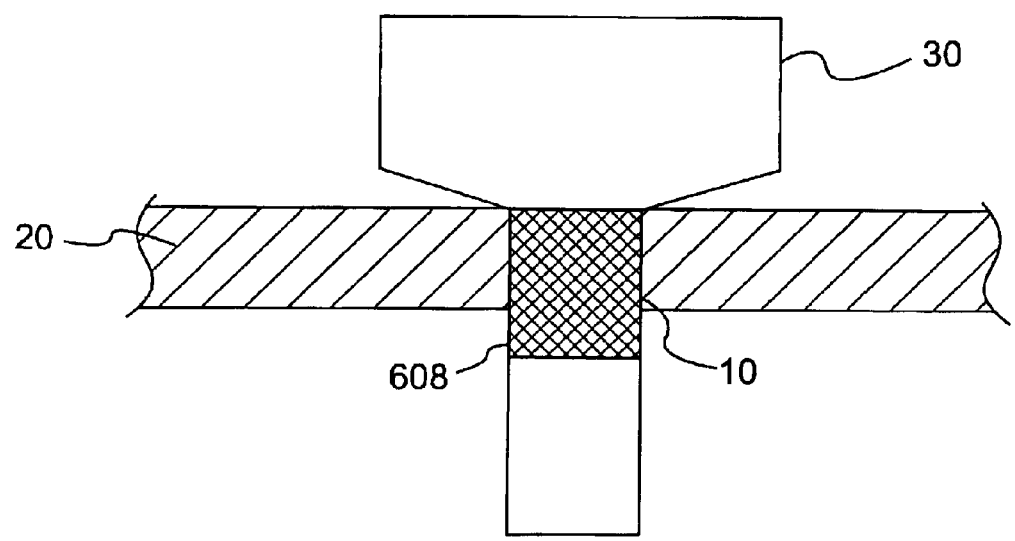
FIG. 26 illustrates the combination of a flexible, woven sleeve and a conventional port.

It is also known to those skilled in the art to insert a sheath around a conventional port to facilitate removal and reinsertion of medical instruments through a patient's incision. In addition, it is also known to provide a sleeve 608 made of a flexible, woven material around the port. An example of such a sleeve 608, in combination with a conventional port 30, is illustrated in FIG. 26. When the port is inserted into the patient, the flexible, woven sleeve 608 is also inserted into the incision at the same time. The flexible, woven sleeve 608 is kept in the patient's incision to facilitate the insertion of instruments into the patient after removal of the initial port.

Although the flexible, woven sleeve 608 can expand, it has a maximum expansion diameter. As a result, if the surgeon tries to insert an instrument in a patient with too great a diameter, the flexible, woven sleeve 608 will prevent the surgeon from inserting the instrument, which could tear the incision. In addition, the flexible, woven sleeve 608 facilitates insertion of instruments into the patient (after the first instrument or port has been removed) by defining a passageway into the patient. As a result, when instruments are introduced into the patient after the placement of the flexible, woven sleeve 608, the instruments are less likely to snag on the patient's tissue or tear the incision due to the angle of insertion. Alternatively, the sleeve 608 may also remain in the incision together with the port throughout the entirety of the surgery.

The embodiments of the LSEP 100, 500 of the present invention are contemplated for use with a flexible, woven sleeve 608. Alternatively, as discussed above, the LSEPs 100, 500 may be used without a flexible, woven sleeve 608 being inserted first into the incision. When intended to be used with a sleeve 608, the sheath of the LSEP 100, 500 should be increased in length relative to the illustrated embodiments so that the prongs may expand when the LSEP 100, 500 is in the expanded position. This is accomplished by adding an intermediate shaft between the holding ring and the prongs. An exemplary embodiment of this construction is described in connection with the apparatus shown, for example, in FIG. 25.

Figure 22:
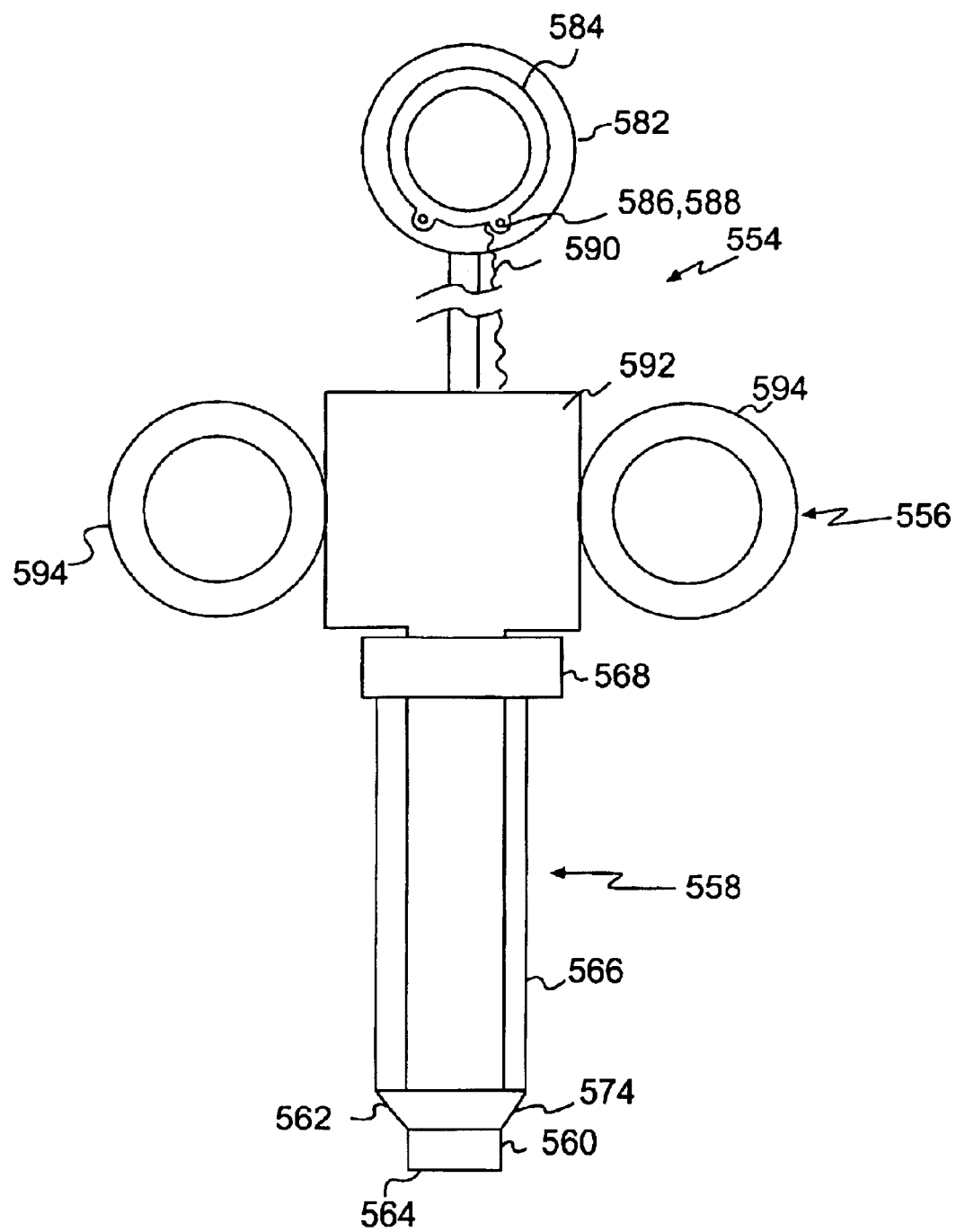
FIG. 22 is a side view of an LSRS according to the teachings of the present invention.

FIG. 22 illustrates a laparoscopic specimen retrieval shoehorn ("LSRS") 554 constructed according to the teachings of the present invention. The LSRS 554 combines the advantages proffered by the sheaths 130, 506 of the LSEPs 100, 500 together with the advantages offered by a modified ERBD. In particular, the LSRS 554 provides an ERBD 556 to which a sheath 558 is connected.

Like the ERBD 520, the LSRS 554 has two operative positions. The first position is the non-deployed state, which is illustrated in FIG. 22. The second position is the deployed position, a representative illustration of which is provided in connection with the discussion of the ERBD 520 shown in FIG. 18. If the non-deployed state, a specimen bag (not shown) is retained in a folded state within a primary shaft 560 of the ERBD 556. The primary shaft 560 includes a forward portion 562, which is enlarged with respect to the tip 564.

In the embodiment illustrated in FIG. 22, the sheath 558 has the same configuration as the sheath 130 illustrated in connection with the LSEP 100. The sheath 558 includes two or more prongs 566 connected to a holding ring 568. The prongs 566 open in the same manner as those illustrated in connection with LSEPs 100, 500.

Figure 23:
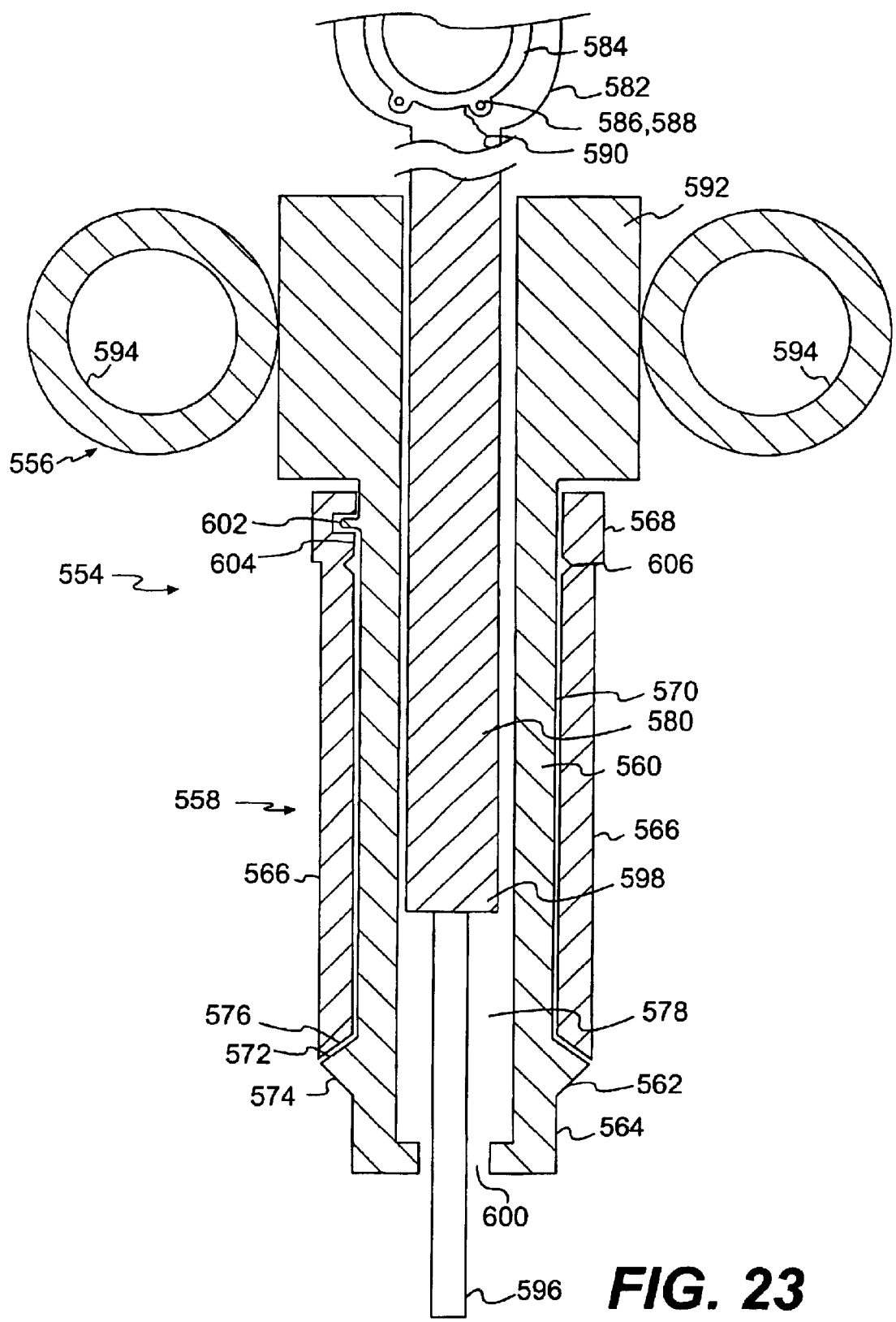
FIG. 23 is a cross-sectional side view of the LSRS illustrated in FIG. 22.

FIG. 23 illustrates the LSRS 554 in cross-section. As indicated above, the LSRS 554 includes a primary shaft 560 around which a sheath 558, having a plurality of prongs 566, is disposed. The sheath 558 is slidably disposed on the primary shaft 560 such that the holding ring 568 may be pushed toward the forward portion 562 of the primary shaft 560.

As illustrated, the forward portion 562 is radially enlarged with respect to the intermediate portion 570 of the primary shaft 560. The forward portion 562 includes a first surface 572 that tapers radially outward from the intermediate portion 570 of the primary shaft 560. The forward portion 562 also includes a second surface 574 that tapers radially inward from the first surface 572. The taper of the first surface 572 preferably matches the taper of the tip 576 of the prongs 566.

As illustrated in FIG. 23, the primary shaft 560 of the LSRS 554 has a bore 578 extending longitudinally therethrough. The secondary shaft 580 of the LSRS 554 is slidably disposed within the bore 578. The secondary shaft 580 is provided with a finger loop 582 at its proximal end. The finger loop 582 is preferably integrally molded with the secondary shaft 580. However, the finger loop 582 may be connected to the secondary shaft 580 in any manner known to those skilled in the art.

A pull ring 584 is removably connected to the finger loop 582 disposed at the distal end of the secondary shaft 580. The pull ring 584 connects to the finger loop 582 via one or more posts 586 that are integrally molded with the finger loop 582. The pull ring 584 includes one or more holes 588 formed therein to engage the posts 586. In this manner, the pull ring 584 may be removably connected to the finger loop 582 until the surgeon wishes to pull on the purse string 590 once connected to the pull ring 584.

At the distal end of the primary shaft 560, the LSRS 554 is provided with a proximal body portion 592. The proximal body portion 592 preferably is molded as a part of the primary shaft 560. The proximal body portion preferably includes at least two finger loops 594, which are connected thereto.

As illustrated in FIG. 23, the secondary shaft 580 includes a flat wire 596 positioned at the distal end 598 thereof. The flat wire 596 preferably is affixed within the distal end 598 such that it is not easily removed therefrom. As would be appreciated by those skilled in the art, the flat wire 596 is not limited solely to a metallic wire with a flat (or rectangular) cross-section. To the contrary, the flat wire 596 may be made from any suitable material and may have any suitable cross-sectional shape such as ovoid, elliptical, or circular, as the particular circumstances dictate.

A specimen bag (not illustrated in FIG. 23) is preferably positioned on the flat wire 596 in the same manner as illustrated in connection with the ERBD 520. When the LSRS 554 is in the non-deployed state, the specimen bag 522 is contained within the bore 578 in the primary shaft 560. To deploy the specimen bag 522, the surgeon pushes the finger loop 582 toward the tip 564 of the primary shaft 560, thereby, forcing the flat wire 596 through an opening 600 at the tip 564 of the primary shaft 560. Since the flat wire 596 is pre-stressed such that it opens into a loop once deployed from the primary shaft 560, the specimen bag 522 opens once the flat wire 596 is pushed through the opening 600.

After a specimen 524 is placed within the specimen bag 522, the sheath 558 is unlocked from the primary shaft 560. As illustrated in FIG. 23, the primary shaft 560 includes a protrusion 602 that is disposed within an L-shaped groove 604 in the holding ring 568 of the sheath 558. The protrusion 602 and groove 604 operate in the same manner as the releasable locking mechanism 310 discussed in connection with the LSEPs 100, 500.

Once unlocked, the sheath 558 is free to slidably move with respect to the primary shaft 560. As discussed in connection with the LSEPs 100, 500, the sheath 558 may be pushed forward toward the distal end 564 of the primary shaft 560. Since the forward portion 562 of the primary shaft tapers outwardly, the forward portion 562 pushes against the interior surfaces of the prongs 566 to force them radially outward. The folding groove 606, provided on the interior surface of the sheath 558 at the transition from the holding ring 568 to the prongs 566, facilitates the outward expansion of the prongs 566 as the primary shaft is pulled out of the patient while the sheath 558 is maintained in its position within the patient.

As would be appreciated by those skilled in the art, the prongs 566 need not be the same type as illustrated in connection with the LSEP 100. Instead, the prongs 566 may be of the shoehorn type illustrated in connection with the LSEP 500. Moreover, other shapes may be employed as would be understood by those skilled in the art without departing from the scope of the present invention.

Figure 24:
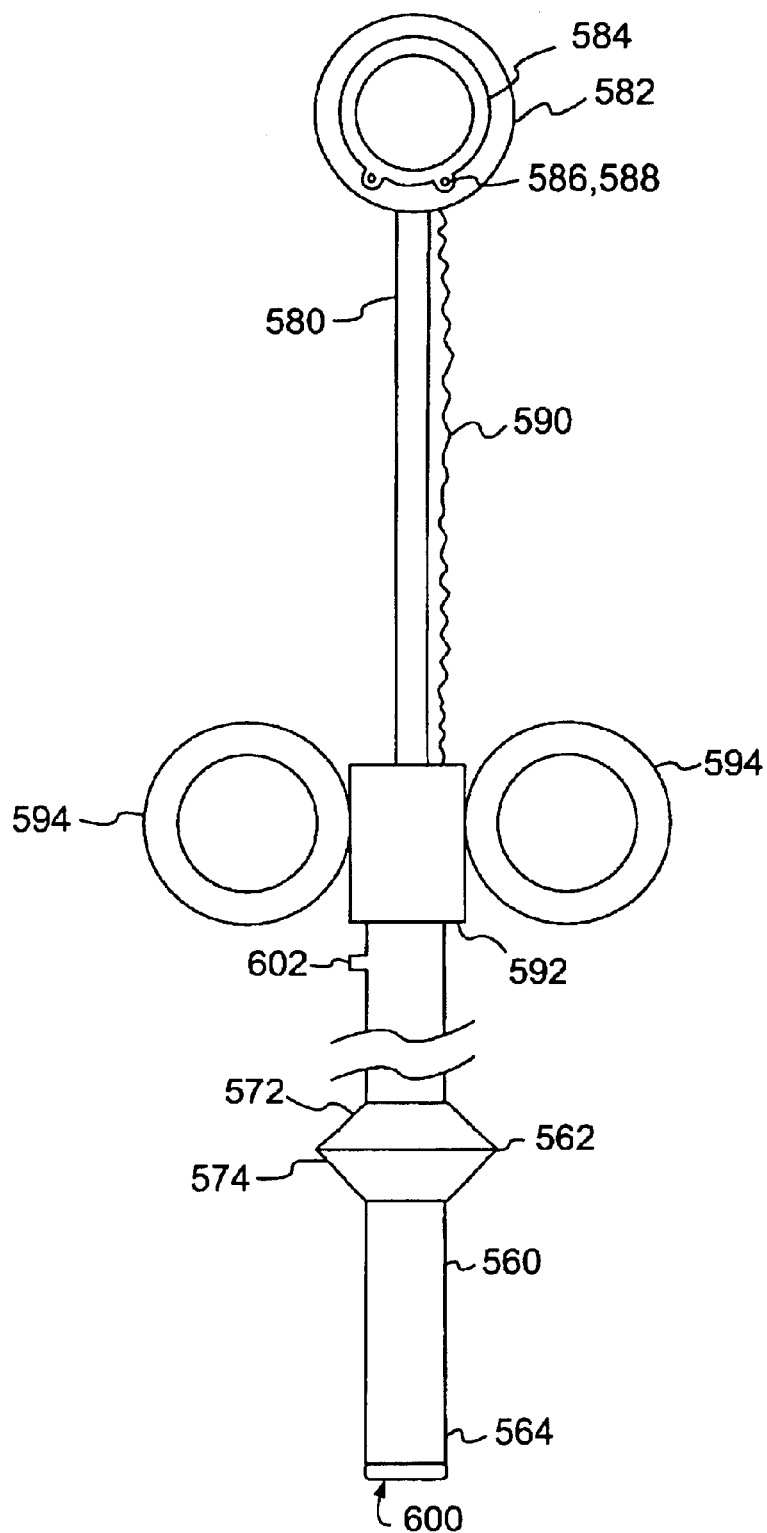
FIG. 24 is a side view illustration of the endoscopic retrieval bag device that forms a part of the LSRS illustrated in FIGS. 22 and 23.

FIG. 24 illustrates the ERBD 556 portion of the LSRS 554 of the present invention. For clarification, the sheath 558 is omitted from this side view. The ERBD 556 portion of the LSRS 554 is shown in the non-deployed condition.

Figure 11:
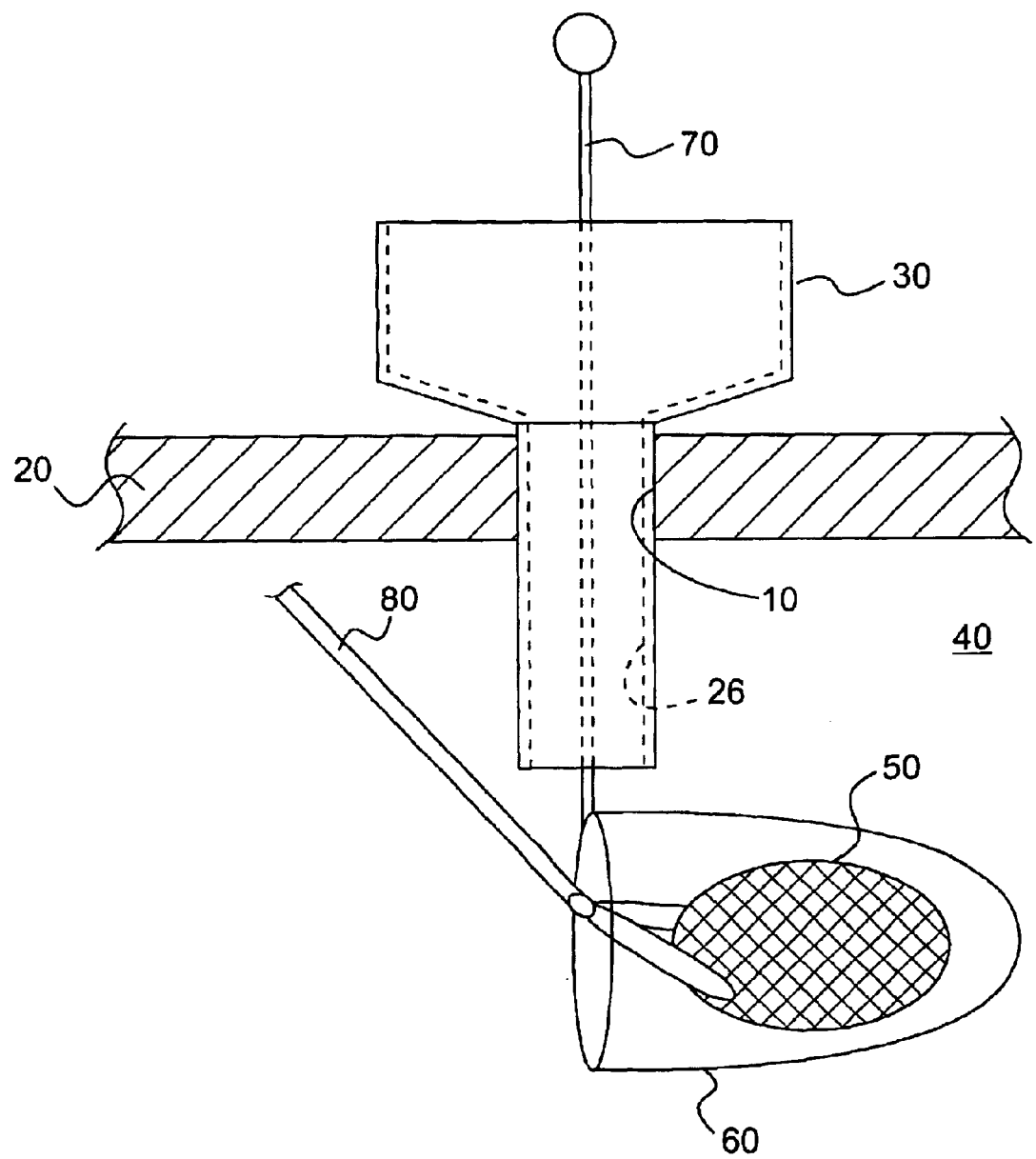
FIGS. 11–14 are side views showing the sequential operation of a conventional LSEP.
Figure 12:
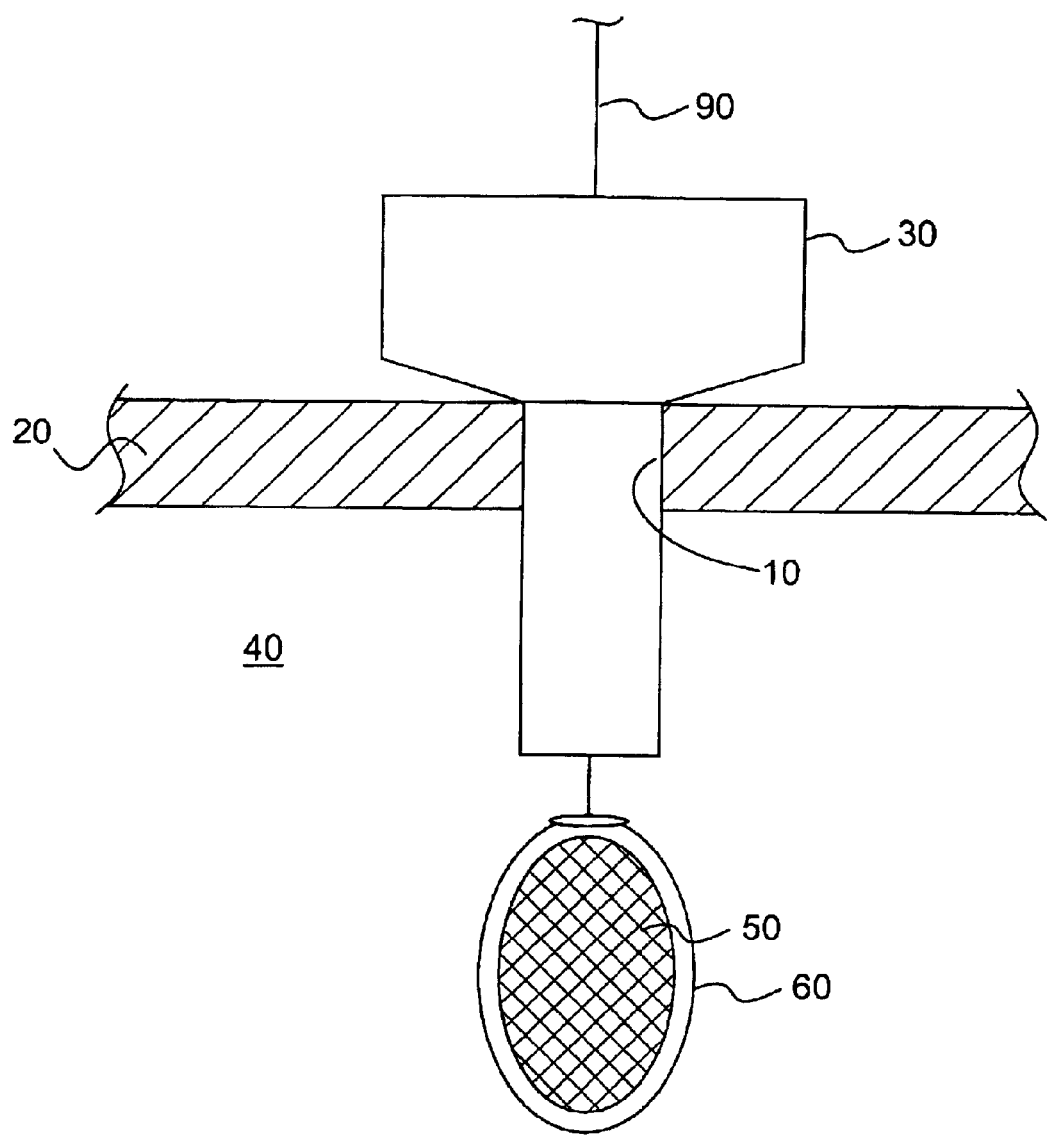
Figure 13:
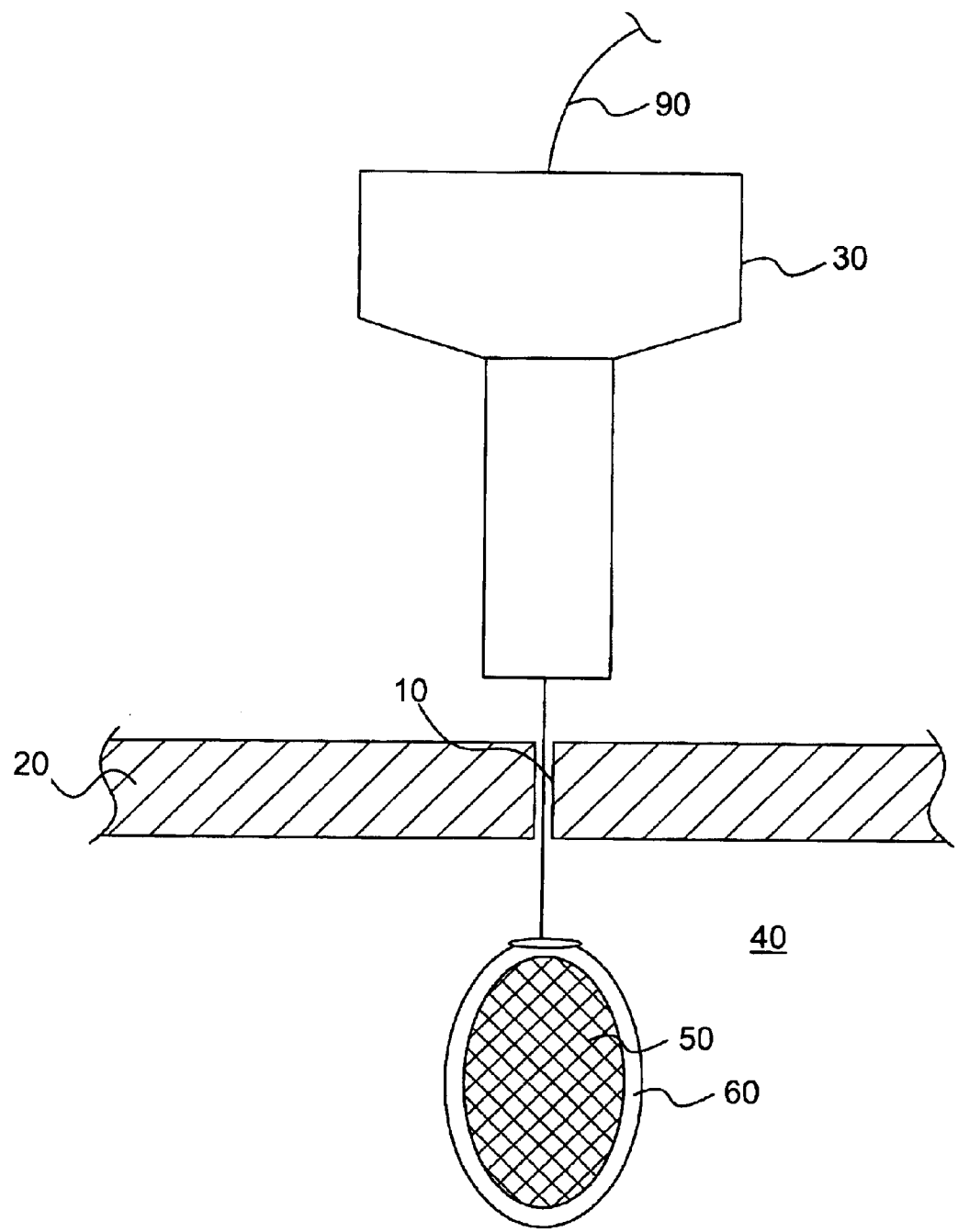
Figure 14:
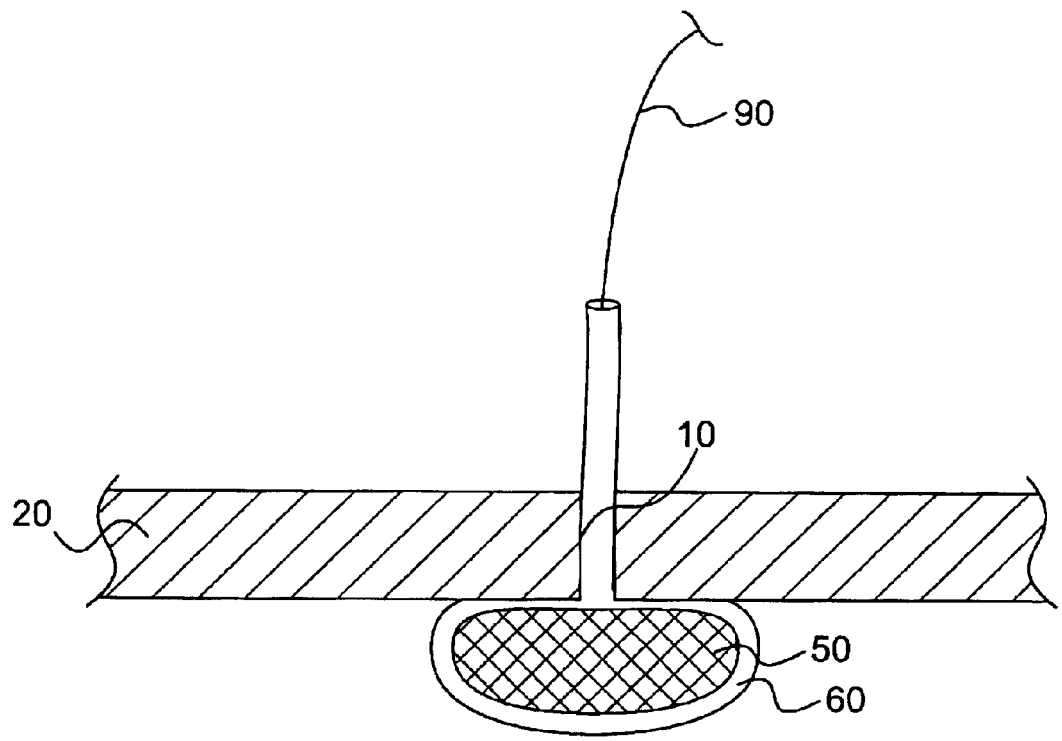

It is further contemplated that the LSRS 554 of the present invention will be used in cooperation with a traditional port, such as the port 30 illustrated in FIGS. 11–13, and/or the flexible woven sleeve 608. If so, the length of the LSRS 554 must be extended so that the operative end of the LSRS 554 may clear the distal end of the port 30 and/or sleeve 608 once positioned within the patient. In other words, the LSRS 554 must be made longer so that the port 30 and/or sleeve 608 does not interfere with the outward expansion of the prongs 566. Preferably, the length of the LSRS 554 is increased by adding a shaft extender between the holding ring 568 and the prongs 566. As would be appreciated by those skilled in the art, the length of the LSRS 554 may be selected to accommodate various different surgery types and operating conditions. Moreover, the length of the LSRS 554 may be increased or decreased to accommodate various sizes of ports 30 and/or sleeves 608 that are commercially available (or that may become commercially available).

Figure 25:
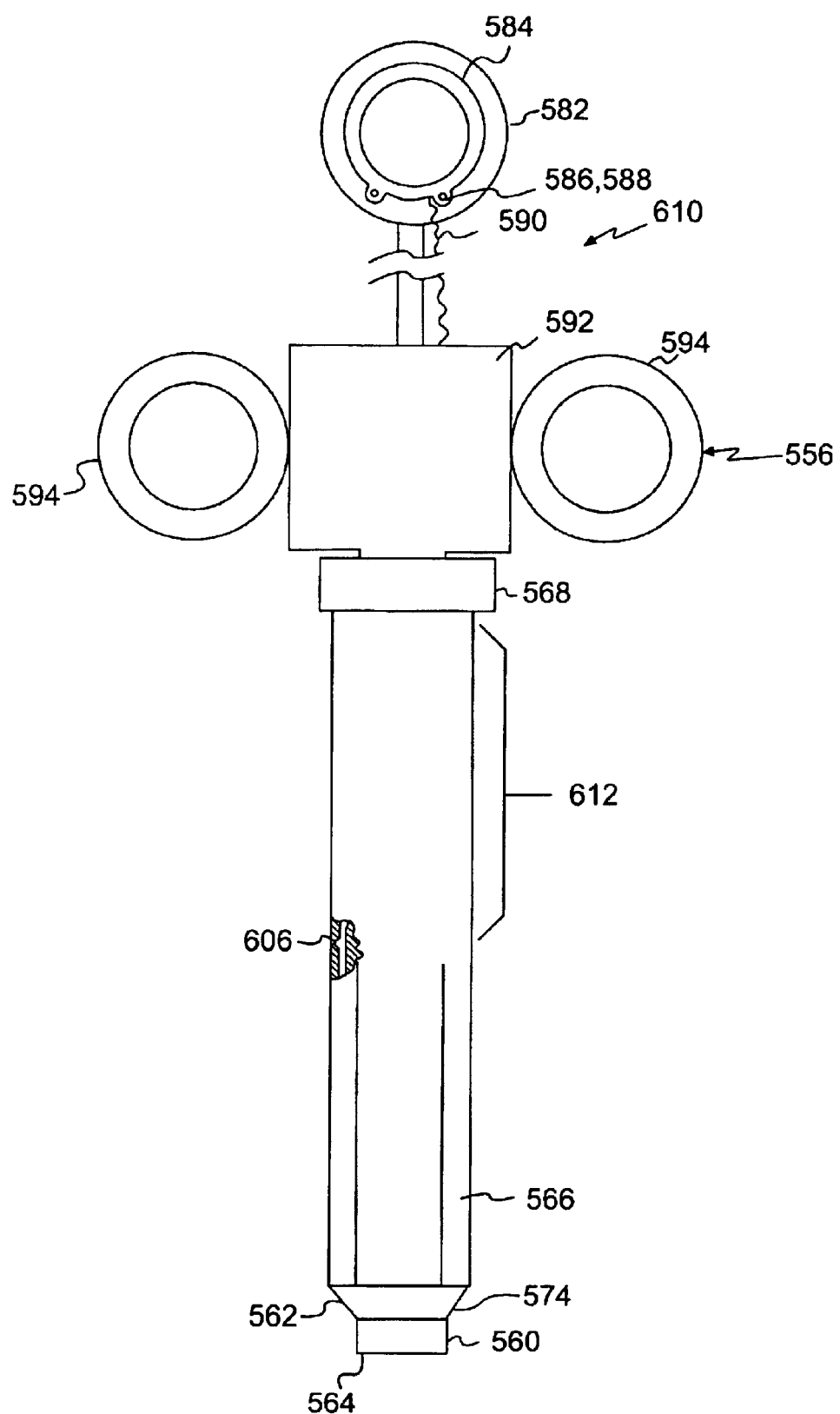
FIG. 25 illustrates another embodiment of the LSRS according to the teachings of the present invention.

FIG. 25 illustrates an LSRS 610 where the length has been extended to accommodate insertion through a port such as the port 30 illustrated in FIGS. 11–13. On the LSRS 610, the prongs 566 are not disposed so that they expand outwardly at a point adjacent to the holding ring 568. Instead, a hollow, intermediate shaft 612 extends a predetermined distance from the holding ring 568 to the prongs 566. As shown in the partial cross-section in FIG. 25, the folding groove 606 has been moved from a position adjacent to the holding ring 568 to the distal portion of the shaft 612. As such, the folding groove 606 has been moved to a position adjacent to the proximal ends of the prongs 566 to facilitate outward expansion of the prongs 566 within the patient. As illustrated, the folding groove is positioned distally to the distal end of the hollow, intermediate shaft 612. As discussed above, the LSRS 610 also may be disposed through a port 30 (or other suitable port) and the shaft 612 preferably is designed for such use.

FIG. 26 illustrates a conventional port 30 with a flexible, woven sleeve 608 disposed around a portion thereof. As discussed above, it is known to insert a port 30 into a sleeve 608 before inserting the port 30 into the patient. During surgery, the port 30 and the sleeve 608 may remain in the patient. Surgical instruments, such as the LSRS 554, may then be inserted through the port 30 as needed.

The foregoing illustrated embodiments are provided to illustrate the structural and functional principles of the present invention and are not intended to be limiting. To the contrary, the principles of the present invention are intended to encompass any and all changes, alterations and/or substitutions within the spirit and scope of the following claims.

What is claimed is:

1. A laparoscopic specimen retrieval shoehorn, comprising:
 a primary shaft, wherein the primary shaft comprises
  a rearward portion,
  an intermediate portion, and
  a forward portion that is radially-enlarged relative to the intermediate portion;
 a secondary shaft slidably disposed within the primary shaft, wherein the secondary shaft comprises an endobag attached thereto; and a sheath, having expanded and contracted positions, slidably disposed around the primary shaft, wherein the sheath comprises a holding ring disposed radially-outwardly from the intermediate portion of the primary shaft, wherein the holding ring is adapted to slide relative to the intermediate portion, the holding ring being disposed at a rear end of the sheath, and a plurality of circumferentially-spaced prongs disposed at a forward end of the sheath, the prongs having forward ends positioned adjacent to the radially-enlarged, forward portion of the primary shaft when in the contracted position and having rearward ends disposed a predetermined distance from the holding ring, wherein, during transition from the contracted to the expanded position, the radially-enlarged forward portion expands the prongs radially-outwardly relative to the primary shaft.

2. A laparoscopic specimen retrieval shoehorn according to claim 1, wherein the prongs are shoehorn shaped and overlap one another at least partially when in the contracted position.

3. A laparoscopic specimen retrieval shoehorn according to claim 1, wherein the sheath further comprises:

an intermediate shaft connecting the holding ring to the rearward ends of the prongs.

4. A laparoscopic specimen retrieval shoehorn according to claim 1, wherein the forward portion of the primary shaft is radially-enlarged relative to an inside surface of the holding ring such that the forward portion prevents the holding ring from sliding forwardly beyond the forward portion.

5. A laparoscopic specimen retrieval shoehorn according to claim 1, further comprising a releasable holding mechanism to selectively secure the holding ring to the intermediate portion of the primary shaft when the sheath is in the contracted position.

6. A laparoscopic specimen retrieval shoehorn according to claim 5, wherein rotation of the holding ring relative to the primary shaft disengages the holding mechanism to allow the sheath to be manipulated into the expanded position.

7. A laparoscopic specimen retrieval shoehorn according to claim 6, wherein the holding mechanism comprises:

a forwardly-facing surface defined by the holding ring;

a notch on an inside surface of the holding ring, the notch extending rearwardly from the forwardly-facing surface; and a protrusion extending from an outer surface of the intermediate portion of the primary shaft, a rearward edge of the protrusion being in front of the forwardly-facing surface when the sheath is in the contracted position to prevent the sheath from moving rearwardly relative to the primary shaft, wherein rotation of the holding ring relative to the primary shaft aligns the protrusion with the notch, thereby allowing the protrusion to move through the notch and the primary shaft to move rearwardly relative to the holding ring to permit the sheath to be manipulated into the expanded position.

8. A laparoscopic specimen retrieval shoehorn according to claim 1, wherein the forward portion of the primary shaft comprises a radially-outwardly-tapering outer surface.

9. A laparoscopic specimen retrieval shoehorn according to claim 8, wherein each prong includes a forward tip that has inside and outside surfaces, and wherein the inside surface of the forward tip tapers radially-outwardly so that, when the sheath is in the contracted position, the outwardly-tapering inside surface of the forward tip of each prong adjoins the outwardly-tapering outer surface of the forward portion of the primary shaft.

10. A laparoscopic specimen retrieval shoehorn according to claim 1, wherein the prongs comprise a flexible material that expands radially-outwardly during expansion of the sheath.

11. A laparoscopic specimen retrieval shoehorn according to claim 10, wherein the prongs comprise at least one of plastic and PVC.

12. A laparoscopic specimen retrieval shoehorn according to claim 1, wherein an indentation is formed on a surface of the sheath to define a folding line for the prongs.

13. A laparoscopic specimen retrieval shoehorn according to claim 1, wherein the prongs are tinted a color easily distinguishable from tissue.

14. A laparoscopic specimen retrieval shoehorn according to claim 1, wherein the prongs are at least partially radio-opaque.

15. A laparoscopic specimen retrieval shoehorn according to claim 1, wherein the secondary shaft further comprises:

a wire attached thereto, the endo-bag being disposed on the wire, wherein the wire is pre-conditioned to form a loop.

16. A laparoscopic specimen retrieval shoehorn according to claim 15, wherein:

the wire has a cross-section selected from a group comprising rectangular, circular, elliptical, and ovoid.

17. A laparoscopic specimen retrieval shoehorn according to claim 1, wherein:

the primary shaft and the secondary shaft define deployed and non-deployed positions with respect to one another, and when in the deployed position, the endo-bag is disposed exteriorly to the primary shaft.

18. A laparoscopic specimen retrieval shoehorn according to claim 15, wherein:

the primary shaft and the secondary shaft define deployed and non-deployed positions with respect to one another, and when in the deployed position, the wire and the endo-bag are disposed exteriorly to the primary shaft.

19. A laparoscopic specimen retrieval shoehorn according to claim 1, further comprising:

a purse string attached to the endo-bag so that, after insertion of a specimen thereinto, the purse string may close an open end of the endo-bag.

20. The laparoscopic specimen retrieval shoehorn of claim 19, wherein:

the endo-bag is detachably connected to the secondary shaft such that, when the purse string is pulled, the endo-bag detaches from the secondary shaft and the open end is closed thereby.

* * * * *